United States Patent
Debevec et al.

(10) Patent No.: US 8,300,234 B2
(45) Date of Patent: Oct. 30, 2012

(54) ESTIMATING SPECTRAL DISTRIBUTION OF REFLECTIONS FROM OBJECT SURFACE BASED ON LOW FREQUENCY ILLUMINATION

(75) Inventors: Paul E. Debevec, Marina del Rey, CA (US); Abhijeet Ghosh, Playa del Rey, CA (US); Pieter Peers, Los Angeles, CA (US); Graham Fyffe, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 286 days.

(21) Appl. No.: 12/803,398

(22) Filed: Jun. 24, 2010

(65) Prior Publication Data

US 2010/0328677 A1  Dec. 30, 2010

Related U.S. Application Data

(60) Provisional application No. 61/220,141, filed on Jun. 24, 2009.

(51) Int. Cl.
*G01B 11/30* (2006.01)

(52) U.S. Cl. ........................................ 356/600
(58) Field of Classification Search .................... None
See application file for complete search history.

(56) References Cited

U.S. PATENT DOCUMENTS

| | | | |
|---|---|---|---|
| 4,145,140 A * | 3/1979 | Fujii | 356/512 |
| 5,764,363 A * | 6/1998 | Ooki et al. | 356/364 |
| 5,835,220 A * | 11/1998 | Kazama et al. | 356/369 |
| 6,965,690 B2 | 11/2005 | Matsumoto | |
| 7,460,216 B2 * | 12/2008 | Lecomte et al. | 356/32 |
| 2003/0011596 A1 | 1/2003 | Zhang et al. | |
| 2007/0018996 A1 | 1/2007 | Wang et al. | |

OTHER PUBLICATIONS

Alldrin, N. et al. 2007. Toward Reconstructing Surfaces With Arbitrary Isotropic Reflectance: A Stratified Photometric Stereo Approach. In Proceedings of the International Conference on Computer Vision (ICCV), 2007, 8 pages.

Alldrin, N. et al. 2008. Photometric Stereo With Non-Parametric and Spatially-Varying Reflectance. In 2008 Conference on Computer Vision and Pattern Recognition (CVPR), Anchorage, Alaska, Jun. 2008, 8 pages.

Debevec, P. et al. 2000. Acquiring the Reflectance Field of a Human Face. In ACM SIGGRAPH 2000, Computer Graphics Proceedings, Annual Conference Series, Jul. 2000, pp. 145-156.

(Continued)

*Primary Examiner* — Tu Nguyen
(74) *Attorney, Agent, or Firm* — McDermott Will & Emery LLP

(57) ABSTRACT

A system for estimating the specular roughness of points on a surface of an object may include a lighting system, an image capture system and a computer processing system. The lighting system may be configured to illuminate the surface of the object at different times with different illumination patterns. Each illumination pattern may illuminate the surface from a plurality of different directions and form an intensity gradient having an order of no more than two. The image capture system may be configured to capture an image of the surface of the object when illuminated by each of the different illumination patterns at each of the different times. The computer processing system may be configured to compute the specular roughness of each point on the surface of the object based on the images captured by the image capture system.

25 Claims, 18 Drawing Sheets
(17 of 18 Drawing Sheet(s) Filed in Color)

OTHER PUBLICATIONS

Georghiades, A.S. 2003. Recovering 3-D Shape and Reflectance From a Small Number of Photographs. In Eurographics Symposium on Rendering, 2003, pp. 230-240.

Holroyd, M. et al. 2008. A Photometric Approach for Estimating Normals and Tangents. In SIGGRAPH Asia '08: ACM SIGGRAPH Asia 2008 papers, 9 pages.

Horn, B.K.P. et al. 1986. The Variational Approach to Shape from Shading. Computer Vision, Graphics, and Image Processing, vol. 33, pp. 174-208.

Ma, W-C. et al. 2007. Rapid Acquisition of Specular and Diffuse Normal Maps from Polarized Spherical Gradient Illumination. In Eurographics Symposium on Rendering, 2007, pp. 183-194.

Mallick, S.P. et al. 2005. Beyond Lambert: Reconstructing Specular Surfaces Using Color. In IEEE Conference on Computer Vision and Pattern Recognition, 2005, 8 pages.

Malzbender T. et al. 2001. SIGGRAPH 2001 Proceedings, Aug. 2001, pp. 519-528.

Ramamoorthi, R. et al. 2002. Frequency Space Environment Map Rendering. In SIGGRAPH 2002, ACM Transactions on Graphics, pp. 517-526.

Sloan, P-P. et al. 2002. Precomputed Radiance Transfer for Real-Time Rendering in Dynamic, Low-Frequency Lighting Environments. In SIGGRAPH 2002, ACM Transactions on Graphics, pp. 527-536.

Wenger, A. 2005. Performance Relighting and Reflectance Transformation With Time-Multiplexed Illumination. In ACM Transactions on Graphics, vol. 24, No. 3, pp. 756-764.

Woodham, R.J. 1980. Photometric Method for Determining Surface Orientation from Multiple Images. Optical Engineering, Jan.-Feb. 1980, vol. 19, No. 1, pp. 139-144.

PCT Application No. PCT/US2010/039787, filed Jun. 24, 2010 (counterpart to U.S. Appl. No. 12/803,398). International Search Report and Written Opinion of the International Searching Authority, mailed Jan. 4, 2011.

* cited by examiner

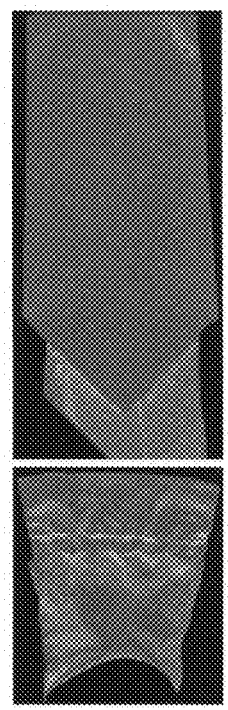 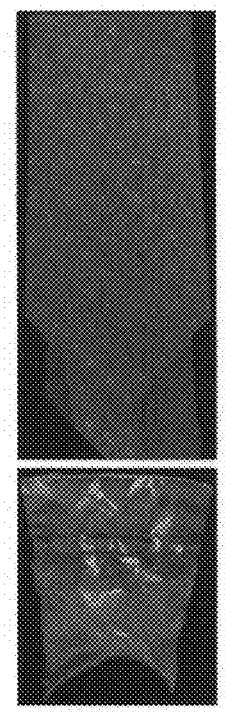 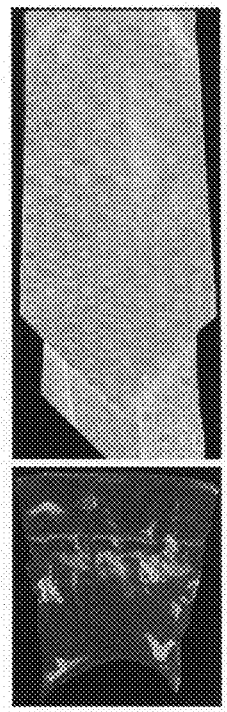 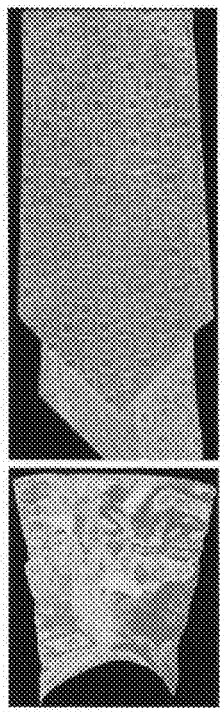
FIG. 6A     FIG. 6B     FIG. 6C     FIG. 6D
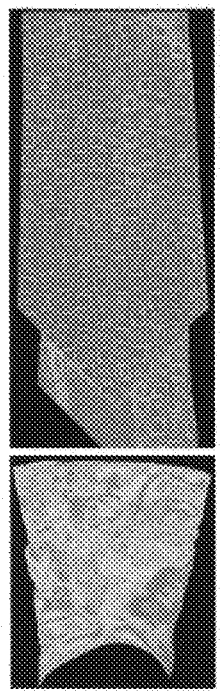 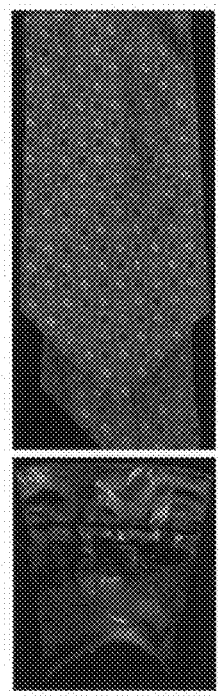 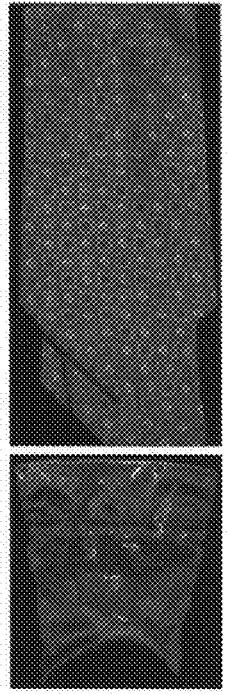
FIG. 6E     FIG. 6F     FIG. 6G

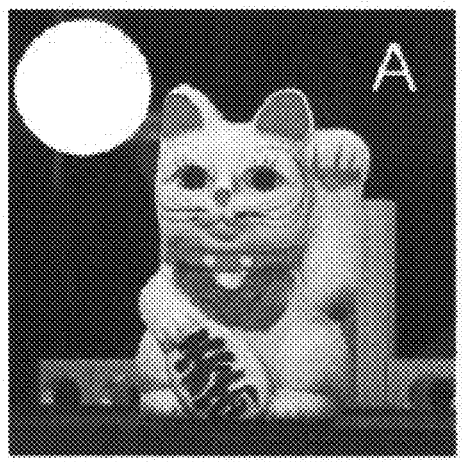
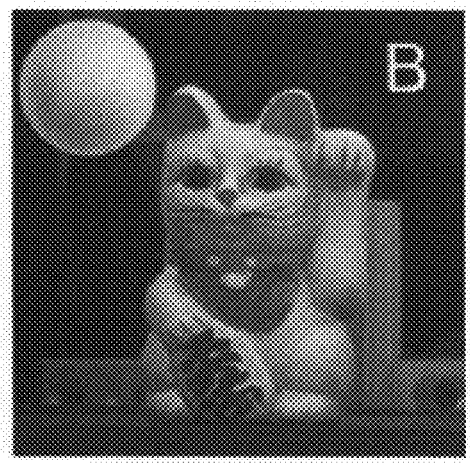
*FIG. 10A*  *FIG. 10B*
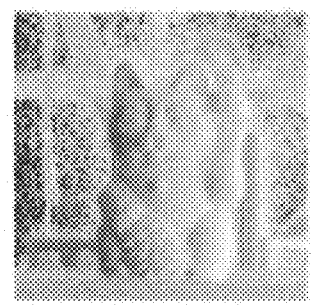
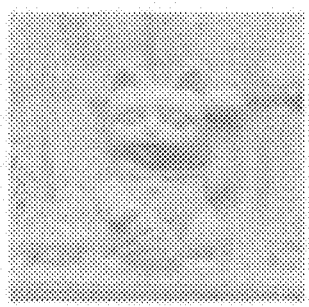
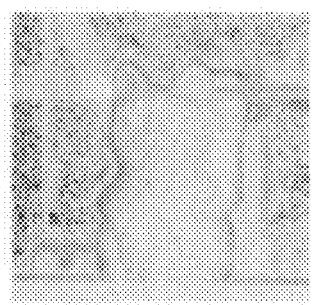
*FIG. 10C*  *FIG. 10D*  *FIG. 10E*
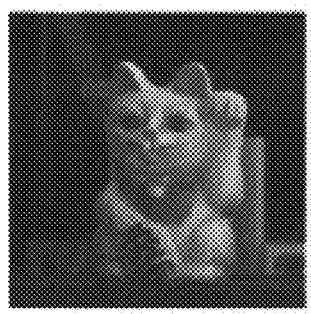
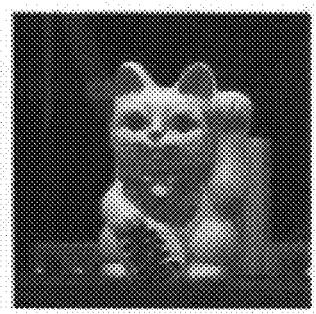
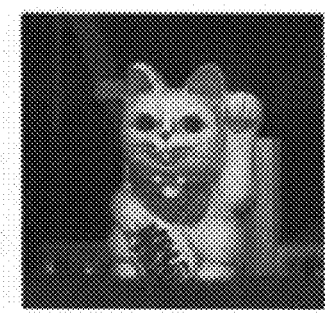
*FIG. 10F*  *FIG. 10G*  *FIG. 10H*

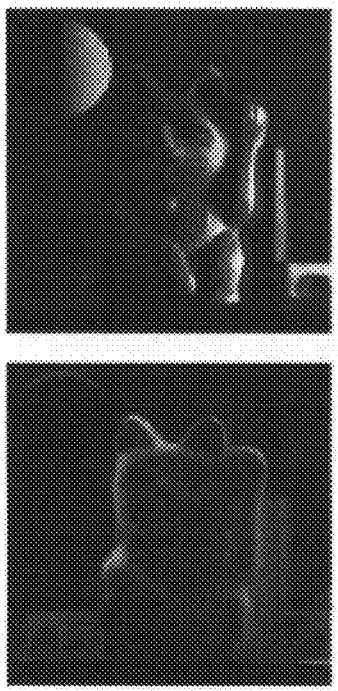
FIG. 18A
FIG. 18D
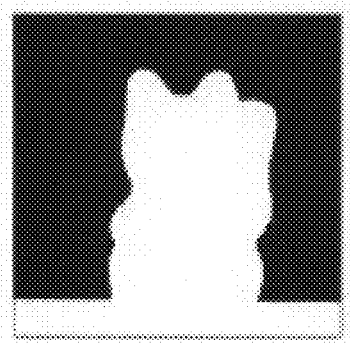
FIG. 18B
FIG. 18C
FIG. 18E
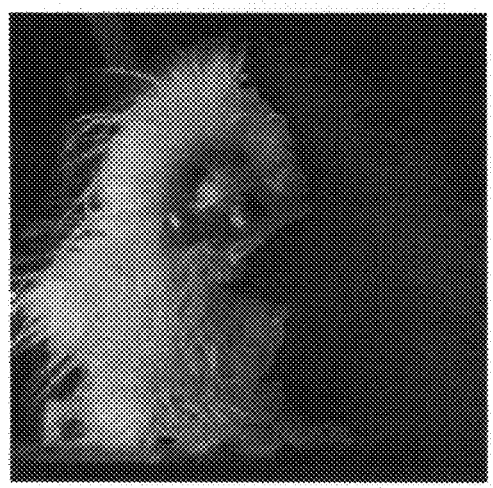
FIG. 19

ESTIMATING SPECTRAL DISTRIBUTION OF REFLECTIONS FROM OBJECT SURFACE BASED ON LOW FREQUENCY ILLUMINATION

CROSS-REFERENCE TO RELATED APPLICATION

This application is based upon and claims priority to U.S. provisional patent application 61/220,141, entitled "ESTIMATING REFLECTANCE DISTRIBUTIONS FROM LOW FREQUENCY ILLUMINATION," filed Jun. 24, 2009. The entire content of this application is incorporated herein by reference.

BACKGROUND

1. Technical Field

This disclosure relates to estimating spectral distributions of reflections from points on an object surface, including specular roughness and tangent vectors.

2. Description of Related Art

Measuring the appearance of real materials may be described by a bidirectional reflectance distribution function (BRDF). See Nicodemus F. E., Richmond J. C., Hsia J. J., Ginsberg I. W., Limperis T, *Geometric considerations and nomenclature for reflectance*, National Bureau of Standards Monograph 160 (1977). The function may be a 4D function that relates the ratio of reflectance between the incident and outgoing directions for a single surface point.

These BRDF models may depend on a sparse set of non-linear parameters that roughly correspond to albedo, specular roughness, surface normal, and tangent directions. Measuring and fitting these parameters for a particular material model may require a dense sampling of incident and outgoing lighting directions. Fitting the parameters of an a-priori chosen BRDF model to observed measurements may rely on complex fragile non-linear optimization procedures.

Some methods may estimate fundamental parameters of appearance, such as normal direction and albedo, without assuming an a-priori material model. Instead they may rely on general properties shared by many physical materials such as symmetry. See Zickler T. E., Belhumeur P. N., Kriegman D. J., *Helmholtz stereopsis: Exploiting reciprocity for surface reconstruction*, Int. J. Comput. Vision 49, 2-3 (2002), 215-227; Alldrin N., Kriegman D., *Toward reconstructing surfaces with arbitrary isotropic reflectance: A stratified photometric stereo approach*, Proceedings of the International Conference on Computer Vision (ICCV) (2007), pp. 1-8; Ma W.-C., Hawkins T., Peers P., Chabert C.-F., Weiss M., Debevec P., *Rapid acquisition of specular and diffuse normal maps from polarized spherical gradient illumination*, Rendering Techniques (2007), pp. 183-194; Alldrin N., Zickler T., Kriegman D., *Photometric stereo with non-parametric and spatially-varying reflectance*, Proceedings of IEEE Computer Vision and Pattern Recognition (CVPR) (2008); Holroyd M., Lawrence J., Humphreys G., Zickler T., *A photometric approach for estimating normals and tangents*, SIGGRAPH Asia '08: ACM SIGGRAPH Asia 2008 papers (2008), pp. 1-9.

The first order spherical statistics of the reflectance under distant illumination may correspond to the normal and reflection vector for diffuse and specular materials respectively. See In Ma W.-C., Hawkins T., Peers P., Chabert C.-F., Weiss M., Debevec P., *Rapid acquisition of specular and diffuse normal maps from polarized spherical gradient illumination*, Rendering Techniques (2007), pp. 183-194. The first order statistics may be efficiently measured using linear gradient illumination conditions. See Ma et al., supra.

The representation and acquisition of the appearance of physical materials and objects may often be classified in two categories: (1) Analytical BRDF-based methods; and (2) Non-parametric and photometric methods.

Analytical BRDF-Based Methods

Analytical material representation BRDF may be designed with certain goals in mind, such as physical accuracy, see Torrance K. E., Sparrow E. M., *Theory of off specular reflection from roughened surfaces*, J. Opt. Soc. Am. 57 (1967), 1104-1114; He X. D., Torrance K. E., Sillion F. X., Greenberg D. P.: *A comprehensive physical model for light reflection*. SIGGRAPH Comput. Graph. 25, 4 (1991), 175-186; facilitating rendering, see Ashikhmin M., Premoze S., Shirley P. S.: *A microfacet-based BRDF generator*. Proceedings of ACM SIGGRAPH 2000 (2000), Computer Graphics Proceedings, Annual Conference Series, pp. 65-74; and versatility and flexibility in approximating physical materials, see Ashikhmin M, Premoze S., Distribution-based BRDFs, Technical Report 2007; Lafortune E. P. F., Foo S.-C., Torrance K. E., Greenberg D. P.: *Non-linear approximation of reflectance functions*. SIGGRAPH '97: Proceedings of the 24th annual conference on Computer graphics and interactive techniques (1997), pp. 117-126; Ward G. J.: *Measuring and modeling anisotropic reflection*. SIGGRAPH Comput. Graph. 26, 2 (1992), 265-272.

Spatially varying appearance; based on the above analytical BRDF models, may be captured to recreate complete digital copies of existing real world objects. See, e.g., Gardner A., Tchou C., Hawkins T., Debevec P.: *Linear light source reflectometry*. ACM SIGGRAPH 2003 (2003), pp. 749-758; Georghiades A.: *Recovering 3-D shape and reflectance from a small number of photographs*. Rendering Techniques (2003), pp. 230Ü-240; Goldman D. B., Curless B., Hertzmann A., Seitz S. M.: *Shape and spatially-varying BRDFs from photometric stereo*. ICCV '05: Proceedings of the Tenth IEEE International Conference on Computer Vision (ICCV'05) Volume 1 (2005), pp. 341-348; Lensch H. P. A., Goesele M., Kautz J., Heidrich W., Seidel H.-P.: *Image-based reconstruction of spatially varying materials*. Proceedings of the 12th Eurographics Workshop on Rendering Techniques (2001), pp. 103-114; Lensch H. P. A., Kautz J., Goesele M., Heidrich W., Seidel H.-P.: *Image-based reconstruction of spatial appearance and geometric detail*. ACM Transactions on Graphics 22, 2 (2003), 234-257; Marschner S.: *Inverse Rendering for Computer Graphics*. PhD thesis, Cornell University, 1998.

Each of these methods may require either a special acquisition device or an acquisition scheme tailored towards a particular prefixed analytical material model. Each may sacrifice spatial variation for angular variation to reduce the total acquisition time. However, the choice of BRDF model may impact the quality of appearance reproduction significantly. See Ngan A., Durand F., Matusik W.: *Experimental analysis of BRDF models*. Proceedings of the Eurographics Symposium on Rendering (2005), pp. 117-226. Furthermore, fitting the model-specific parameters may be complicated and ill-conditioned due to the non-linear nature of the parameters and the presence of measurement noise. It may only become clear after attempting to fit the measured data that the choice of material model may be suboptimal.

Switching to a better suited BRDF model after the fact may be difficult due to the inherent reliance of the acquisition setup/scheme of these methods on a particular model.

Non-Parametric and Photometric Techniques

Classical photometric stereo, see Woodham R. J.: *Photometric stereo: A reflectance map technique for determining surface orientation from image intensity*. Proc. SPIE's 22nd Annual Technical Symposium (1978), vola 155, may estimate surface normals by assuming an underlying Lambertian material, and by using a small set of fixed viewpoint observations under point lighting. However, most materials may not be purely Lambertian, and thus an inaccurate surface normal may be estimated. As a result, photometric stereo has been extended to non-Lambertian materials. See, e.g., Georghiades A.: *Recovering* 3-*D shape and reflectance from a small number of photographs*. Rendering Techniques (2003), pp. 230Ü-240; Goldman D. B., Curless B., Hertzmann A., Seitz S. M.: *Shape and spatially-varying brdfs from photometric stereo*. ICCV '05: Proceedings of the Tenth IEEE International Conference on Computer Vision (ICCV'05) Volume 1 (2005), pp. 341-348. While these methods may handle a wider range of material types, they still may rely on (mostly isotropic) analytical BRDF models that limit their generality.

To overcome this limitation, a number of techniques have been proposed that may avoid using parametric BRDF models. See Mallick S. P., Zickler T. E., Kriegman D. J., Belhumeur P. N.: Beyond lambert: *Reconstructing specular surfaces using color*. Proc. IEEE Conf. Computer Vision and Pattern Recognition (2005). Mallick et al. reduce a general material to Lambertian by removing the specular "component," and subsequently apply traditional photometric stereo. Hertzmann and Seitz estimate surface normals using a reference object with known shape and similar material properties as the target object. See Hertzmann A., Seitz S.: *Shape and materials by example: a photometric stereo approach*. Computer Vision and Pattern Recognition, 2003. Proceedings. 2003 IEEE Computer Society Conference on 1 (2003), 533-540, vol. 1. While this method may not rely on parametric appearance models, it may require a reference object which is not always available.

Another class of methods may exploit general properties of surface reflectance to infer surface statistics. A common assumption is that the maximum reflectance is observed when the halfway vector coincides with the surface normal. See, e.g., Francken Y., Cuypers T., Mertens T., Gielis J., Bekaert P.: *High quality mesostructure acquisition using specularities*. Computer Vision and Pattern Recognition, 2008. CVPR 2008. IEEE Conference on (2008), 1-7). Various forms of symmetry may constitute another property that has been exploited. Zickler et al. exploit the Helmholtz reciprocity to recover depth and normal directions. See Zickler T. E., Belhumeur P. N., Kriegman D. J.: Helmholtz stereopsis: *Exploiting reciprocity for surface reconstruction*. Int. J. Comput. Vision 49, 2-3 (2002), 215-227. Alldrin and Kriegman exploit the symmetry about the view-normal plane in case of isotropic BRDFs. See Alldrin N., Kriegman D.: *Toward reconstructing surfaces with arbitrary isotropic reflectance: A stratified photometric stereo approach*. Proceedings of the International Conference on Computer Vision (ICCV) (2007), pp. 1-8; Ma et al. assume symmetry about the mean vector of a BRDF observed from a fixed viewpoint. See Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194. They show that for Lambertian reflections the mean may correspond to the surface normal, and for specular reflections to the reflected direction. Both may be efficiently and directly measured by using polarized spherical gradient illumination. Holroyd et al. assume a similar type of symmetry, but use a dense sampling to resolve both the normal direction as well as tangent vectors per surface point. See Holroyd M., Lawrence J., Humphreys G., Zickler T.: *A photometric approach for estimating normals and tangents*. In SIGGRAPH Asia '08: ACM SIGGRAPH Asia 2008 papers (2008), pp. 1-9.

While these methods may not rely on a parametric model, they may not provide complete information regarding the surface reflectance. Lawrence et al. used inverse shade trees and an optimization scheme coined ACLS to decompose the spatially varying material properties of planar samples from dense hemispherical samplings in a collection of 1D curves and 2D textures. See Lawrence J., Ben-Artzi A., Decoro C., Matusik W., Pfister H., Ramamoorthi R., Rusinkiewicz S.: *Inverse shade trees for non-parametric material representation and editing*. ACM Transactions on Graphics 25, 3 (2006), 735-745. Alldrin et al. also employ ACLS to compute bivariate representations of isotropic surface appearances, including surface normals. See Alldrin N., Zickler T., Kriegman D.: *Photometric stereo with non-parametric and spatially-varying reflectance*. Proceedings of IEEE Computer Vision and Pattern Recognition (CVPR) (2008). Zickler et al. share reflectance information from different surface points to create a dense nonparametric reconstruction of appearance. See Zickler T., Ramamoorthi R., Enrique S., Belhumeur P. N.: *Reflectance sharing: Predicting appearance from a sparse set of images of a known shape*. IEEE Trans. Pattern Anal. Mach. Intell. 28, 8 (2006), 1287-1302.

Image-Based Relighting

Image-based relighting is a technique for synthesizing images of a scene under novel illumination conditions, based on a set of input photographs. In its most basic form, images of a scene may be acquired, see Paul Haeberli, *Synthetic lighting for photography*, January 1992, or rendered, see Jeffry S. Nimeroff, Eero Simoncelli, and Julie Dorsey, *Efficient re-rendering of naturally illuminated environments*, Fifth Eurographics Workshop on Rendering, June 1994, pp. 359-373. under a set of basis lighting conditions. Then, a relit version of the scene may be produced by taking linear combinations of the basis lighting conditions, akin to compositing together different lighting passes of a model miniature.

Debevec et al. used a light stage device to acquire a dataset of a human face lit by a dense set of over two thousand lighting directions on the sphere, and showed that such datasets could be efficiently illuminated under novel real-world lighting conditions such as high dynamic range lighting environments through image-based relighting. See Paul Debevec, Tim Hawkins, Chris Tchou, Haarm-Pieter Duiker, Westley Sarokin, and Mark Sagar, *Acquiring the reflectance field of a human face*, Proc. ACM SIGGRAPH 2000, Computer. Graphics Proceedings, Annual Conference Series, July 2000, pp. 145-156. Recent work in the area of pre-computed radiance transfer has shown that pre-rendering an object's reflectance under basis illumination conditions may allow for real-time relighting as it moves through interactive environments. See Peter-Pike Sloan, Jan Kautz, and John Snyder, *Precomputed radiance transfer for real-time rendering in dynamic, lowfrequency lighting environments*, ACM Transactions on Graphics 21 (2002), no. 3, 527-536; Ravi Ramamoorthi and Pat Hanrahan, *Frequency space environment map rendering*, ACM Transactions on Graphics 21 (2002), no. 3, 517-526; Rui Wang, John Tran, and David Luebke, *All-frequency interactive relighting of translucent objects with single and multiple scattering*, ACM Transactions on Graphics 24 (2005), no. 3, 1202-1207. Basis illumination datasets have also been shown to be useful for object recognition, see R. Ramamoorthi, *Modeling Illumination*

*Variation with Spherical Harmonics*, Face Processing: Advanced Modeling Methods, 2006, pp. 385-424, including for faces.

A benefit to image-based relighting techniques may be that complex illumination effects including spatially-varying diffuse and specular reflection, self-shadowing, mutual illumination, and subsurface scattering may be all encoded within the data and thus may appear accurately in the renderings. Traditional techniques may require far more advanced reflectometry and light transport simulation. Drawbacks may include that a lot of data must be acquired and stored. This may make the techniques less practical for capturing dynamic subjects. For example, high-speed video at thousands of frames per second may be required for dynamic subjects, as in Andreas Wenger, Andrew Gardner, Chris Tchou, Jonas Unger, Tim Hawkins, and Paul Debevec, *Performance relighting and reflectance transformation with timemultiplexed illumination*, ACM Transactions on Graphics 24 (2005), no. 3, 756-764), and for memory-efficient relighting as hundreds of images may be required.

Efficient representations of Image-Based Relighting datasets has been explored for rendering, generally by focusing on efficient representations for the scene's per-pixel reflectance functions.

Debevec et al. estimated diffuse and specular albedos and normals for each pixel's reflectance function, reducing the information for each pixel from hundreds of reflectance measurements to just a few reflectance parameters. See Paul Debevec, Tim Hawkins, Chris Tchou, Haarm-Pieter Duiker, Westley Sarokin, and Mark Sagar, *Acquiring the reflectance field of a human face*, Proc. ACM SIGGRAPH 2000, Computer Graphics Proceedings, Annual Conference Series, July 2000, pp. 145-156. However, these parameters attempted to factor out global illumination effects, which may require these effects to be simulated later and may forfeit the elegance and realism of image based relighting.

Malzbender et al. fit quadratic polynomial texture maps (PTMs) to reflectance functions consisting of fifty lighting directions across the hemisphere. See Tom Malzbender, Dan Gelb, and Hans Wolters, *Polynomial texture maps*, Proc. SIGGRAPH 2001, pp. 519-528. The PTMs may greatly reduce the reflectance data to a compact, data-driven representation, and resulting renderings may produce realistic and relatively smooth and diffuse renditions of the objects under varying illumination. However, the technique may still require a dense set of incident lighting directions to be recorded. Its consideration may also have been restricted to lighting originating from the front hemisphere, which may be a significant limitation for fully three-dimensional objects.

Ma et al. used a computational illumination approach to modeling reflectance functions using a small number of incident lighting conditions. See Wan-Chun Ma, Tim Hawkins, Pieter Peers, Charles-Felix Chabert, Malte Weiss, and Paul Debevec, *Rapid acquisition of specular and diffuse normal maps from polarized spherical gradient illumination*, Rendering Techniques 2007: 18th Eurographics Symposium on Rendering, June 2007, pp. 183-194. Using a spherical light stage and a set of four spherical gradient illumination conditions derived from the 0th and 1st-order spherical harmonics, the technique may directly measure the magnitude (albedo) and centroid (surface normal) of each pixel's reflectance function. These measurements may be used to drive a Lambertian or Phong reflectance lobe to represent the reflectance function; using polarization difference imaging, the diffuse and specular components may be modeled independently. As with PTMs, the resulting renderings may still encode most of the effects of global illumination. However, the lobe widths may need to be selected manually (either choosing a Lambertian lobe or a Phong specular exponent), as no reflectance lobe width information may be derived from the measurements.

All of the above methods may either require a dense sampling of the lighting directions, integrate information over multiple surface points, or deliver incomplete appearance information.

SUMMARY

Specular roughness and tangent vectors, per surface point, may be estimated from polarized second order spherical gradient illumination patterns. For isotropic BRDFs, only three second order spherical gradients may be sufficient to robustly estimate spatially varying specular roughness. For anisotropic BRDFs, an additional two measurements may yield specular roughness and tangent vectors per surface point. Different illumination configurations may be used which project both discrete and continuous fields of gradient illumination. A direct estimate of the per-pixel specular roughness may not require off-line numerical optimization that has otherwise been used for the measure-and-fit approach to classical BRDF modeling.

An image-based method may relight a scene by analytically fitting cosine lobes to the reflectance function at each pixel, based on gradient illumination photographs. Realistic relighting results for many materials may be obtained using a single per pixel cosine lobe obtained from just two color photographs: one under uniform white illumination and the other under colored gradient illumination. For materials with wavelength-dependent scattering, a better fit may be obtained using independent cosine lobes for the red, green, and blue channels, obtained from three achromatic gradient illumination conditions instead of the colored gradient condition.

There may be two cosine lobe reflectance functions, both of which allow an analytic fit to the gradient conditions. One may be nonzero over half the sphere of lighting directions, which may work well for diffuse and specular materials, but may fail for materials with broader scattering such as fur. The other may be non-zero everywhere, which may work well for broadly scattering materials and may still produce visually plausible results for diffuse and specular materials.

An approximate diffuse/specular separation of the reflectance may be performed, and scene geometry may be estimated from the recovered photometric normals to produce hard shadows cast by the geometry, while still reconstructing the input photographs exactly.

A system for estimating the specular roughness of points on a surface of an object may include a lighting system, an image capture system and a computer processing system. The lighting system may be configured to illuminate the surface of the object at different times with different illumination patterns. Each illumination pattern may illuminate the surface from a plurality of different directions and form an intensity gradient having an order of no more than two. The image capture system may be configured to capture an image of the surface of the object when illuminated by each of the different illumination patterns at each of the different times. The computer processing system may be configured to compute the specular roughness of each point on the surface of the object based on the images captured by the image capture system.

The lighting system may be configured such that some of the illumination patterns have an intensity gradient having an order of two. The computer processing system may be configured to compute the specular roughness of each point on the surface of the object based on the images captured by the image capture system while the surface is illuminated by the illumination patterns which have an intensity gradient having an order of two.

The lighting system may include a linear polarizer configured to linearly polarize the illumination patterns that have an intensity gradient having an order of two.

The image capture system may include a linear polarizer configured to linearly polarize the images of the surface of the object. The linear polarizer may be configured to be user-adjustable so as to controllably change the direction of the polarization of the images of the surface of the object.

The surface of the object may be substantially isotropic. The lighting system may be configured such that three of the illumination patterns have an order of two. The computer processing system may be configured to compute the specular roughness of each point on the surface of the object based on the images captured by the image capture system under the illumination of only three illumination patterns having an order of two. The lighting system may be configured such that four of the illumination patterns have an order of one. The computer processing system may be configured to compute the specular roughness of each point on the surface of the object based on the images captured by the image capture system under the illumination of only four illumination patterns having an order of one.

The surface of the object may be substantially anisotropic. The lighting system may be configured such that five of the illumination patters have an order of two. The computer processing system may be configured to compute the specular roughness and a tangent vector of each point on the surface of the object based on the images captured by the image capture system under the illumination of only five illumination patterns having an order of two. The lighting system may be configured such that four of the illumination patters have an order of one. The computer processing system may be configured to compute the specular roughness and the tangent vector of each point on the surface of the object based on the images captured by the image capture system under the illumination of only four illumination patterns having an order of one.

The lighting system may include a substantially flat LCD display, a plurality of light sources arranged in a hemispherical array, and/or a plurality of light sources arranged in a spherical array.

The computer processing system may be configured to directly compute the variance $\sigma^2$ from a total energy for each point on the surface of the object based on the images captured by the image capture system by substantially computing $$\frac{L_2}{L_0} - \frac{L_1^2}{L_0^2},$$

where $L_0$ is the image of the object acquired under a constant spherical illumination condition, $L_1$ is the image acquired under a linear gradient illumination condition, and $L_2$ is the image acquired under a quadratic gradient illumination condition.

The lighting system may be configured such that all of the images on which the computation of specular roughness is based were illuminated with an illumination pattern having an intensity gradient having an order of no more than one.

The computer processing system may be configured to compute a reflectance function at each point and to analytically fit a cosine lobe to each reflectance function.

The cosine lobe may be a hemispherical cosine lobe of substantially the form $f(\Theta)=k(\hat{\alpha}\cdot(\Theta))^n$, where $\Theta$ is a direction, k is the overall intensity of the cosine lobe, $\hat{\alpha}$ is the axis of the cosine lobe, and n is the exponent of the cosine lobe.

The cosine lobe may be a spherical cosine lobe of the substantially form $$f(\Theta) = k\left(\frac{1}{2}\hat{\alpha}\cdot\Theta + \frac{1}{2}\right)^n,$$

where $\Theta$ is a direction, k is the overall intensity of the cosine lobe, $\hat{\alpha}$ is the axis of the cosine lobe, and n is the exponent of the cosine lobe.

The computer processing system may be configured to compute a color channel for each point and for each point and each color channel for each point substantially $o_w$, $o_x$, $o_y$, where $o_w$ is the image of the object acquired under a constant spherical illumination condition, $o_x$ is the image of the object acquired under a linear gradient illumination condition aligned left-to-right, $o_y$ is the image of the object acquired under a linear gradient illumination condition aligned bottom-to-top, and $o_z$ is the image of the object acquired under a linear gradient illumination condition aligned back-to-front.

The lighting system may be configured such that one of the illumination patterns has a single color gradient and wherein the computer processing system is configured to substantially synthesize $o_x$, $o_y$, by $o_x=o_w\times$red channel of $o_c$/red channel of $o_w$, $o_y=o_w\times$green channel of $o_c$/green channel of $o_w$, and $o_z=o_w\times$blue channel of $o_c$/blue channel of $o_w$, where $o_w$ is the image of the object acquired under a constant spherical illumination condition, and $o_c$ is the image of the object acquired under a linear color gradient illumination condition, with the gradation of red illumination aligned left-to-right, the gradation of green illumination aligned bottom-to-top, and the gradation of blue illumination aligned back-to-front.

The computer processing system may be configured to compute specular roughness substantially based on the following equation:

$$n = \frac{2\|\alpha\| - o_w}{o_w - \|\alpha\|},$$

where $\alpha=(2o_x-o_w, 2o_y-o_w, 2o_z-o_w)$, $o_w$ is the image of the object acquired under a constant spherical illumination condition, $o_x$ is the image of the object acquired under a linear gradient illumination condition aligned left-to-right, $o_y$ is the image of the object acquired under a linear gradient illumination condition aligned bottom-to-top, and $o_z$ is the image of the object acquired under a linear gradient illumination condition aligned back-to-front.

The computer processing system may be configured to compute specular roughness substantially based on the following equation:

$$n = \frac{2\|\alpha\|}{o_w - \|\alpha\|},$$

where $\alpha=(2o_x-o_w, 2o_y-o_w, 2o_z-o_w)$, $o_w$ is the image of the object acquired under a constant spherical illumination condition, $o_x$ is the image of the object acquired under a linear gradient illumination condition aligned left-to-right, $o_y$ is the image of the object acquired under a linear gradient illumination condition aligned bottom-to-top, and $o_z$ is the image of the object acquired under a linear gradient illumination condition aligned back-to-front.

The lighting system may be configured such that one of the illumination patterns has an intensity gradient having an order of zero and one of the illumination patterns has an intensity gradient having an order of one. The computer processing system may be configured to compute the specular roughness of each point on the surface of the object based on the images captured by the image capture system under the illumination of only the illumination pattern with an intensity gradient having an order of one and the illumination pattern having an intensity gradient having an order of zero.

The computer processing system may be configured to directly compute the specular roughness of each point on the surface of the object based on the images captured by the image capture system without fitting data which is representative of the images to an appearance model.

Non-transitory computer readable storage media may contain computer-readable programming instructions. When read and executed by a computer system, these instructions may cause the computer system to compute the specular roughness of each point on a surface of an object based on images of the surface of the object. Each image may be of the surface of the object while illuminated at a different time by a different illumination pattern. Each illumination pattern may of any of the types discussed above.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

FIGS. 6A-6G shows results of specular reflectance parameter estimation on two anisotropic samples.

FIGS. 10A-10H illustrate a cat subject photographed under the full-on (FIG. 10A) and colored gradient (FIG. 10B) illumination conditions. FIGS. 10C-10E illustrate the red, green, and blue components of the ratio of FIG. 10B to FIG. 10A. FIGS. 10F-10H illustrate FIGS. 10C-10E multiplied by FIG. 10A.

FIGS. 18A-18E illustrate how a user-supplied visibility mask (center) reduces unwanted shadows.

FIG. 19 illustrates that the visibility masking assumption does not hold for highly scattering materials such as the duck subject, resulting in an inappropriately hard shadow terminator.

DETAILED DESCRIPTION OF ILLUSTRATIVE EMBODIMENTS

Figure 1A:
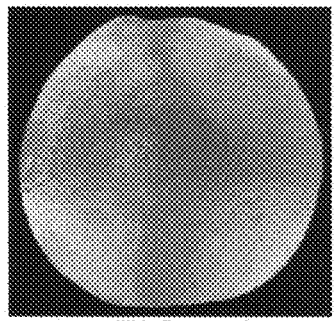
FIGS. 1A-1E illustrate specular reflectance properties of a plastic orange estimated using polarized second order spherical gradient illumination conditions.
Figure 1B:
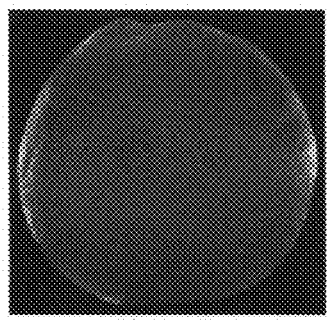
Figure 1C:
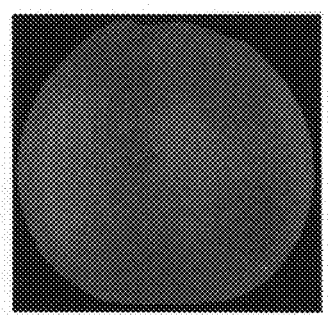
Figure 1D:
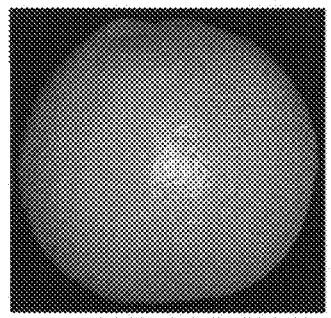
Figure 1E:
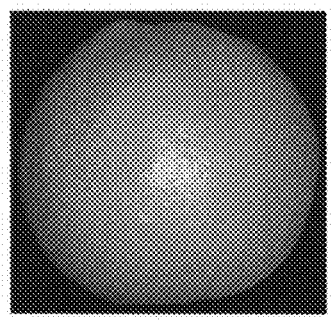

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

A per-pixel specular roughness may be estimated using polarized second order spherical gradients that provide measurements of the variance about the mean (i.e., reflection vector).

For isotropic BRDFs, only three additional axis-aligned second order spherical gradient illumination patterns may be sufficient for a robust estimate of per pixel specular roughness.

FIG. 1 illustrates specular reflectance properties of a plastic orange estimated using polarized second order spherical gradient illumination conditions. FIG. 1A illustrates specular normals; FIG. 1B illustrates specular albedo; FIG. 1C illustrates specular roughness; FIG. 1D illustrates a rendering; and FIG. 1D is a photograph of the orange. The estimated specular roughness map in FIG. 1C may be used as the per-pixel distribution for a Torrance-Sparrow BRDF to create the rendering in FIG. 1D that may closely match the validation photograph in FIG. 1E.

By using five second order spherical harmonics, related to the second order spherical gradient illumination patterns, reliable estimates of the specular roughness and tangent directions of general anisotropic BRDFs may be made. Using a lookup table, these estimated high order statistics may then be directly translated to the parameters of any BRDF model of choice.

An example of a direct application of this method is the estimation of spatially varying reflectance parameters of arbitrary objects. The method may rely on only up to nine distinct illumination conditions with minimal capture time. It may be amenable to capturing per-surface point roughness parameters of human subjects.

The method may enable the acquisition of general appearance statistics per surface point without prior knowledge of the object geometry and without assuming a preselected BRDF model. The acquisition scheme may be fast and optimized to capture these general statistics, which may then be subsequently mapped to most analytical BRDF parameter spaces.

The method may capture the second order statistics of surface reflection independently per surface point. These second order statistics may correspond to specular roughness and the tangent vectors for specular reflections. These statistics may be readily captured by extending the linear spherical gradients of Ma et al. (cited above) with second order spherical gradients. As such, it may require only a few observations, while delivering statistics suitable for creating complete appearance descriptions.

Theoretical Background

This section introduces notations and definitions that may be used to infer specular roughness and anisotropy from second order gradient illumination. The definitions of moments on general 1D functions are re-caped and then extended to a spherical domain. How these moments may be used to infer specular roughness is then shown. The connection between spherical harmonics and spherical moments is then shown, along with how they may be used to measure and infer roughness and anisotropy.

0th, 1st, and 2nd Moments

In statistics the zeroth, first and second moments of a general 1D function f(x) may correspond to the total energy $\alpha$, mean $\mu$, and variance $\sigma^2$ of that function. These moments may be directly computed from the innerproducts of the function f(x) and a constant function (g(x)=1), linear gradient (g(x)=x), and quadratic function (g(x)=$x^2$), denoted by $L_0$, $L_1$, and $L_2$ respectively:

$$\alpha = \int f(x)dx, \quad (1)$$
$$= L_0.$$

$$\mu = \int x \frac{f(x)}{\alpha} dx, \quad (2)$$
$$= \frac{1}{\alpha} \int xf(x)dx,$$
$$= \frac{L_1}{L_0}.$$

$$\sigma^2 = \int (x-\mu)^2 \frac{f(x)}{\alpha} dx, \quad (3)$$
$$= \frac{1}{\alpha} \left( \int x^2 f(x)dx - 2\mu \int xf(x)dx + \mu^2 \int f(x)dx \right),$$
$$= \frac{1}{\alpha}(L_2 - 2\mu L_1 + \mu^2 L_0),$$
$$= \frac{L_2}{L_0} - \frac{L_1^2}{L_0^2}.$$

0th, 1st, and 2nd Spherical Moments

These moments may be extended to the spherical domain by redefining $L_0$, $L_1$, and $L_2$ on the sphere $\Omega$. This may be compactly denoted using the following vector notation:

$$L_0 = \int_\Omega f(\overline{\omega})d\overline{\omega}, \quad (4)$$

$$L_1 = \int_\Omega \overline{\omega} f(\overline{\omega})d\overline{\omega}, \quad (5)$$

$$L_2 = \int_\Omega \overline{\omega}\overline{\omega}^T f(\overline{\omega})d\overline{\omega}, \quad (6)$$

where $\overline{\omega}$ [$\omega_x$, $\omega_y$, $\omega_z$] $\ni \Omega$ and each integration is with respect to solid angle. Thus: $\omega_x^2 + \omega_y^2 + \omega_z^2 = 1$. Note that $\overline{\omega}\overline{\omega}^T$ may be the generalization of the quadratic function $x^2$ to the spherical domain, and may be a symmetric 3×3 matrix. Furthermore $L_0$ may be a scalar, $L_1$ may be a vector of length 3, and $L_2$ may be a 3×3 symmetric matrix. Applying these to Equations (1), (2), and (3), may yield the 0th, 1st, and 2nd order spherical moments. The three linear spherical gradient of Ma et al. Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194 may correspond to $\overline{\omega}$. Likewise, $\overline{\omega}\overline{\omega}^T$ may define six new second order spherical gradients. On the diagonal of this matrix may be the quadratic gradients $\omega_x^2$, $\omega_y^2$, and $\omega_z^2$. On the off-diagonal elements may be the mixed linear gradients: $\omega_x\omega_y$, $\omega_x\omega_z$, and $\omega_y\omega_z$.

Specular Roughness

Ma et al. demonstrated that for specular reflections, the zeroth and first order moments may correspond to the specular albedo and reflection vector. See Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194. The second moment under specular reflections may be directly proportional to specular roughness. Note that this "specular roughness" may be independent of a chosen analytical BRDF model. While the exact relation to a particular BRDF model's specular parameters may be highly model dependent, it may still be instructive to verify the correlations of the 2nd moment and the specular parameters of an analytical model. For example, consider the Ward BRDF Ward G. J.: *Measuring and modeling anisotropic reflection*. SIGGRAPH Comput. Graph. 26, 2 (1992), 265-272:

$$R(\vec{h}) = c \cdot e^{\left(\frac{h_x}{h_z \sigma_x}\right)^2 + \left(\frac{h_y}{h_z \sigma_y}\right)^2}, \quad (7)$$

where c is a normalization constant, $\vec{h} = (h_x, h_y, h_z)$ is the halfway vector between incident $\overline{\omega}_i$ and outgoing $\overline{\omega}_o$ directions, and $\sigma_x$ and $\sigma_y$ are the anisotropic specular roughness parameters. By definition, R may be normalized, and consequently $\alpha=1$. For simplicity, assume that the local shading frame (reflected direction+tangent directions) are known, and the spherical gradients are defined in this frame (this may be accomplished by an appropriate rotation such that the reflection direction is aligned with [0,0,1]). Then, μ=[0,0,1]. In this case Equation (3) may simplify to $\sigma^2=L_2$, and:

$$L_2 = \int_\Omega \bar{\omega}\bar{\omega}^T R(\bar{\omega})d\bar{\omega} \sim \begin{pmatrix} \sigma_x^2 & 0 & 0 \\ 0 & \sigma_y^2 & 0 \\ 0 & 0 & \sigma_z^2 \end{pmatrix}. \quad (8)$$

Intuitively, Equation (7) may closely resemble a normal distribution for which the 2nd moment corresponds to the variance (the diagonal elements). The off-diagonal element in $L_2$ may be zero because the gradients are axis aligned. Note that $\sigma_z^2$ may depend on the values of $\sigma_x^2$ and $\sigma_y^2$. The exact value of $\sigma_z^2$ may not have a direct physical meaning, hence this value may be ignored. Practically, the above states that the observed radiance may be proportional to the specular roughness, when illuminating a surface point with shading frame aligned quadratic gradients $\omega_x^2$ and $\omega_y^2$.

2nd Order Spherical Harmonics

The above discussion may assume that the gradients are aligned with the local shading frame. However, this shading frame may most likely not known beforehand. Furthermore, every surface point may have a potentially different shading frame orientation. Additionally, the six second order spherical gradients may not form an orthogonal spherical basis, and as such may not be optimal in terms of number of patterns. Ideally, the responses under some optimal (i.e., orthogonal) canonical spherical basis illumination may be captured, from which the responses of gradients aligned with the local shading frame may be computed during processing for each surface point.

A well known set of orthogonal spherical basis functions are spherical harmonics. Spherical harmonics may be thought of as the spherical generalization of Fourier functions Sloan P.-P., Kautz J., Snyder J.: *Precomputed radiance transfer for real-time rendering in dynamic, lowfrequency lighting environments*. SIGGRAPH '02: Proceedings of the 29th annual conference on Computer graphics and interactive techniques (2002), pp. 527-536. An interesting property of spherical harmonics may be that they are invariant under rotation, similar to how Fourier functions are invariant under translation. While the first order spherical gradients may correspond exactly to the first order spherical harmonics Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194, second order spherical gradient may not correspond exactly to the second order spherical gradients (i.e., there may be six second order spherical gradients, but only five second order spherical harmonics). However, there may be some overlap, in particular, the second order spherical harmonic that only depends on the azimuthal angle may correspond exactly to $\omega_z^2$ (up to a scale factor, and assuming that the azimuthal angle is defined with respect to the $\omega_z=1$ axis). Due to the rotation invariance, rotations of spherical harmonics may be just linear combinations of the same functions. See Sloan P.-P., Kautz J., Snyder J.: *Precomputed radiance transfer for real-time rendering in dynamic, lowfrequency lighting environments*. SIGGRAPH '02: Proceedings of the 29th annual conference on Computer graphics and interactive techniques (2002), pp. 527-536. Thus, $\omega_z$ may be aligned to any axis using only rotations. As a result, any second order spherical gradient (including $\omega_x^2$ and $\omega_y^2$) may be expressed using second order spherical harmonics only.

Practically, this may imply that, by capturing the response of a surface point under second order spherical harmonic illumination, the response of that surface point would be under any second order spherical gradient due to linearity of light transport may be computed. Furthermore, the rotation from world coordinates to shading frame may be solely determined by the reflected direction and the tangent directions. As shown by Ma et al. Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194, the reflected direction corresponds to the first moment (acquired using linear spherical gradients). The tangent directions may then be defined as the other two principal vectors of the specular lobe. Let the reflected vector correspond to the Z axis of some rotated frame with arbitrary orthogonal X and Y axes. It may be unlikely that the tangent directions will exactly correspond to these arbitrary X and Y axes. However, the responses of the second order spherical gradients $\omega_x^2$ and $\omega_y$ in this frame may still be computed. Furthermore, computing the response under $\omega_z \omega_y$ may allow the creation of a 2×2 covariance matrix. Computing the principal vectors of this covariance matrix may yield the tangent directions. The magnitude of these principal vectors correspond to $\sigma_x^2$ and $\sigma_y^2$.

If the underlying material is isotropic, then the exact orientation of the tangent vectors may not matter, and $\sigma_x=\sigma_y$. In this case, any rotated frame (with Z corresponding to the reflected direction) may be sufficient to compute the specular roughness, and thus only $\omega_x^2$ may need to be computed for an arbitrary X axis orthogonal to Z. This may allow the specular roughness to be captured using a subset of just three second order spherical harmonics. These may be the spherical harmonics that are proportional to $Z^2$, $X^Z$ and $X^2-Y^2$ (i.e., m={0,−2,+2}), omitting the spherical harmonics proportional to XY and YZ (i.e., m={+1,−1}). The spherical harmonics frame may then be rotated such that the Z axis may be perpendicular to the reflected direction. The computed response of this rotated $Z^2$ spherical harmonics may correspond to the isotropic specular roughness.

The above analysis may ignore the effects of Fresnel reflections, masking and shadowing, foreshortening, and albedo. As in Ma et al. Ma W.-C., Hawkins T., Peers P., Chabert C.-F., Weiss. M., Debevec P.: *Rapid acquisition of specular and diffuse normal maps from polarized spherical gradient illumination*. Rendering Techniques (2007), pp. 183-194, foreshortening may be assumed to vary little over the specular lobe, and thus may be considered a constant scale factor. The effects of the albedo may be compensated by dividing by the zeroth moment (i.e., albedo). unless special precautions are taken, the Fresnel effects may be "baked" into the zeroth moment, and thus a division by the zeroth moment may also compensate for the Fresnel effects on the second moment. Masking and shadowing may be "baked" into the second moment as well.

Error Analysis

This section analyzes the accuracy and limits of estimating specular roughness and anisotropy by the techniques described herein. The effects of Fresnel reflectance and cosine factors in the estimation of specular roughness is also analyzed. For this purpose, simulations of the effects of second order spherical gradient illumination were carried out on analytic BRDFs (Ward and Ashikhmin) with various roughness parameters.

Figure 2A:
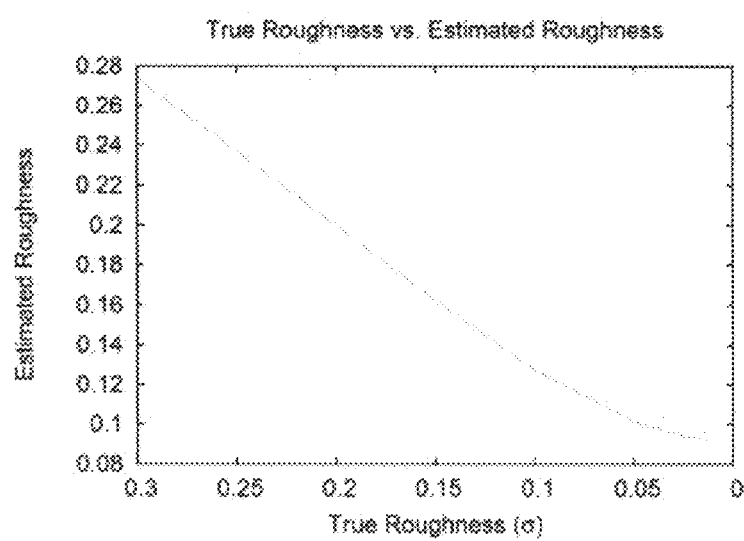
FIGS. 2A and 2B illustrate a simulation of estimated specular roughness using second order spherical gradient illumination for various roughness parameters.
Figure 2B:
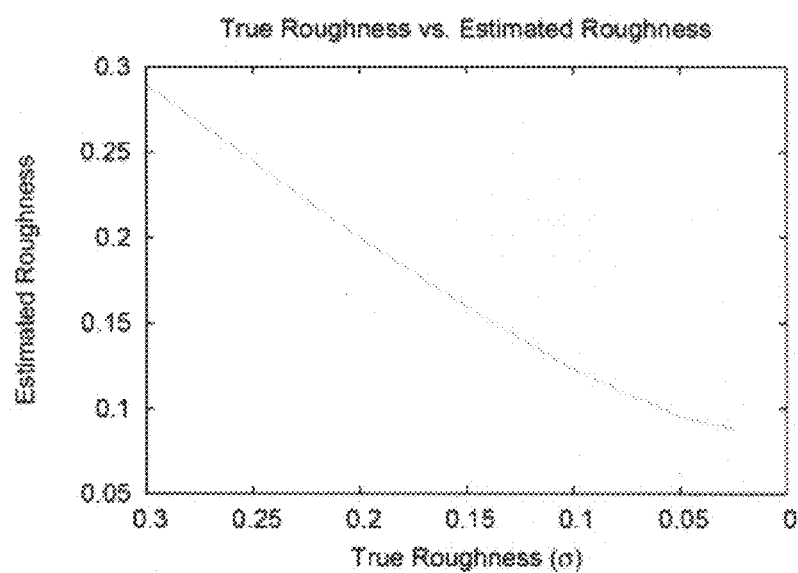

FIGS. 2A and 2B illustrate a simulation of estimated specular roughness using second order spherical gradient illumination for various roughness parameters. FIG. 2A demonstrates that the roughness estimation for the Ward BRDF model is indeed linearly proportional as predicted by Equation (8), and may be accurate up to roughness $\sigma=0.1$, beyond which the method overestimates the computed roughness due to the finite resolution of the simulation. For highly specular BRDFs, there may be very little difference in the computed integrals over the specular lobe for the first and second order spherical gradients which impacts the precision of the estimate. FIG. 2B shows a similar plot for the Ashikhmin BRDF model with Fresnel reflectance $F_0=0.1$, demonstrating that the division by the zeroth term may remove any Fresnel effects from the specular roughness estimation. This is also seen in real acquired data in FIGS. 3A-3C.

Figure 3A:
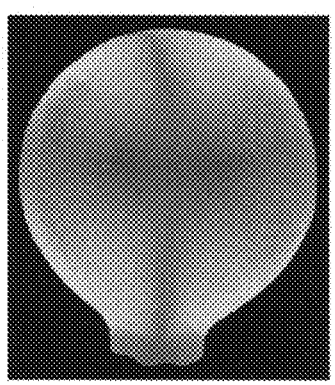
FIGS. 3A-3C illustrate viewpoint independence of the estimated specular roughness for a glossy ornament.
Figure 3B:
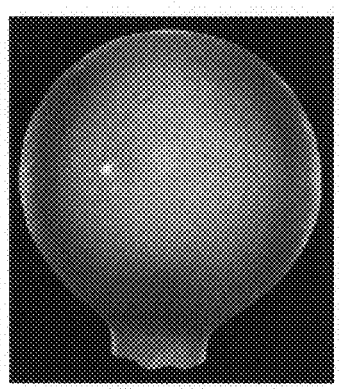
Figure 3C:
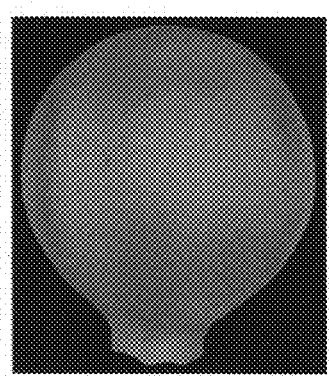

FIGS. 3A-3C illustrate viewpoint independence of the estimated specular roughness for a glossy ornament. FIG. 3A illustrates specular normals; FIG. 3B illustrates specular albedo; and FIG. 3C illustrates specular roughness. The division by the albedo may remove any Fresnel effects at grazing angles.

Simulations also found the cosine factor to not have any significant effect on the roughness estimate.

Figure 4A:
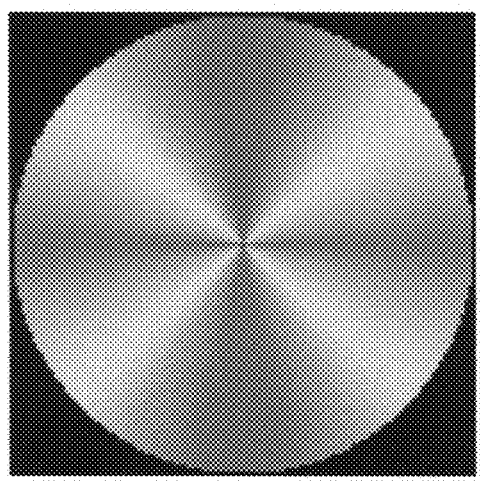
FIGS. 4A and 4B illustrate simulation of tangent frame estimation for a flat anisotropic disk with rotating tangent frame.
Figure 4B:
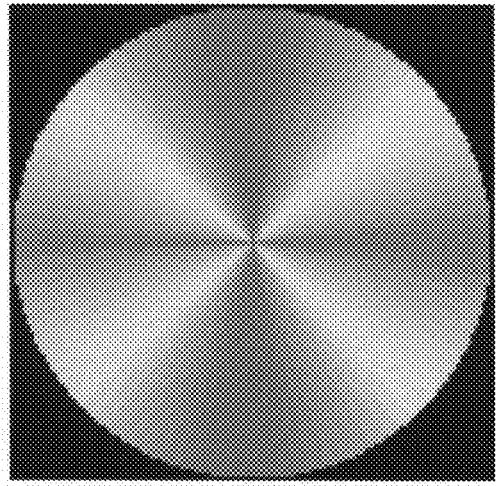

FIGS. 4A and 4B illustrate simulation of tangent frame estimation for a flat anisotropic disk with rotating tangent frame. The simulation, may use an anisotropic Ward BRDF with roughness parameters $\sigma_x=0.3$ and $\sigma_y=0.1$. FIG. 4A illustrates a true tangent, while FIG. 4B illustrates an estimate tangent. The recovery of the tangents of an anisotropic BRDF is demonstrated by FIGS. 4A and 4B.

Measurement and Analysis

In this section the theory derived in the section above is applied to the measurement of specular roughness (and tangent vectors) of physical objects. The different measurement setups and calibration is discussed first. Next, the algorithms for computing the roughness and tangent vectors are discussed. Finally, an analysis on the required lighting resolution of the measurement setups is discussed before presenting the results of several acquired objects in a section below.

Measurement Setup and Calibration

Three different measurement setups may be employed to illustrate the effectiveness of the methods described herein. Using each of the three devices, an object may be illuminated using the zeroth (i.e., constant), first (i.e., linear), and second order spherical gradients. Depending whether or not the target object only contains isotropic reflections, 3 or all 5 second-order spherical gradients may be emitted. This may yield a total of 7 and 9 illumination conditions, respectively.

The first setup may consist of an LED sphere with approximately 150 individually controllable lights. Each light may be covered with a linear polarizer in the pattern of Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194. The object placed at the center of the sphere may be observed through a polarized camera placed outside the sphere. The effects of the gradient illumination patterns on the object may be recorded under both cross and parallel polarization conditions in order to separate the diffuse and specular reflections. A linear polarizer on the camera may be configured to be adjusted to provide these different polarizations.

The second setup may use a substantially flat LCD monitor as a controllable light source. The object of interest may be placed at a small distance from the LCD screen, aimed such that all reflections observed through the camera from the object see the LCD screen. Because the monitor covers only a small part of the full sphere of incident directions, the exact mapping from LCD pixel to incident lighting direction on the object may be carefully calibrated. This may be achieved by placing a mirrored sphere at the location of the object, and computing a one-to-one correspondence between pixels on the sphere (i.e., directions) and pixels on the LCD. Even though the LCD monitor may not cover the full sphere of incident directions, and thus the spherical illumination patterns may not be completely emitted onto the object, a correct estimate of the second order statistics may still be made as long as the solid angle extended by the specular reflection from a surface point is completely included in the projected solid angle of the LCD monitor seen from the respective surface point. In such a case, the observed radiance may be the result of illumination incident from the extended solid angle, and thus from a portion of the LCD monitor. Any illumination or lack thereof outside this extended solid angle may not influence the observed radiance for that surface point. Due to the limited angular support of specular BRDFs, this condition may be met by restricting the normal directions for which roughness parameters may be estimated. Diffuse and specular reflection may be separated, by exploiting the linear polarization of the LCD screen, and capturing the effects of each gradient pattern under a large set of (camera) polarization orientations. The maximum and minimum observed (per-pixel) intensities over the different polarization orientations may correspond to the parallel and cross polarized observations, respectively.

The third setup may be a rough specular hemisphere similar to Peers P., Hawkins T., Debevec P.: *A Reflective Light Stage*. Tech. Rep. ICT Technical Report ICT-TR-04.2006, ICT-USC, 2006. The object may be placed near the center of the hemisphere, next to a projector equipped with a fish-eye lens. The object may be observed through a hole in the apex of the hemisphere. Light emitted by the projector may be reflected by the hemisphere onto the object, and subsequently observed by the camera. A similar geometric calibration as above may be performed to ensure a one-to-one mapping between directions and projector pixels. Separate diffuse and specular reflections may not be separated using this setup. The objects placed in this setup may be restricted to ones exhibiting specular reflections only.

The first setup may have the advantage that it covers the full sphere of incident lighting directions, and thus may deal with objects of any geometry. The second setup may be the most restrictive in this case, and may be mostly suited for planar surfaces. In terms of separating the diffuse from the specular reflections, the first device may by far the easiest (only two photographs per lighting pattern are needed), followed by the second device. Due to the limited sampling density of the first device, it may only be suited for objects with materials exhibiting rough specular reflections. The other two devices may have a very dense sampling, and may deal with almost any type of specular reflection.

Practical Methodology

First discussed is how to compute specular roughness and tangent vectors from measurements in the various setups described above. For isotropic materials, in principle, only measurements under 7 illumination conditions may be required. This assumes that the first and second order spherical gradients may be steered to the appropriate directions as discussed in a section above. However, in practice this may not be possible depending upon the measurement setup. The LCD panel setup and the reflective dome may not cover the entire sphere of directions and hence may not be suited for spherical harmonics based rotations. For such setups, the specular roughness may be approximated as the magnitude of the roughness measured along the orthogonal X and Y directions:

$$\sigma^2 = \|\sigma_x^2 + \sigma_y^2\|, \quad (9)$$

where the reflection vector is aligned with the Z direction. This may be a reasonable approximation for surfaces that are mostly flat. In order to enforce symmetry on the above approximation, both the X and Y aligned first order gradients and the corresponding reverse gradients may be measured. The second order X and Y spherical gradients may be symmetric, by definition, about these axes. This may still lead to a total of 7 illumination conditions for such measurement setups. When computing the specular roughness according to Equation 3 with these measurements, a chose may be made between the first order gradients and the reverse gradients depending upon the orientation of the reflection vector.

Measurements with the LED sphere setup, on the other hand, may take advantage of the spherical harmonic rotations to compute the specular roughness more accurately according to the procedure discussed in a section above. For anisotropic materials, in order to recover the tangent vectors in practice, a search may be made for the local X and Y orientations with the largest anisotropy $$\left(\frac{\sigma_x}{\sigma_y}\right).$$

To relate the estimated model-independent roughness parameter to a particular model specific parameter, one of the following two strategies may be followed. For model specific parameters that are linearly dependent on the variance, the corresponding scale factor may be pre-computed. For non-linear dependencies (e.g., the sharpness parameter for the Blinn-Phong BRDF), the non-linear mapping function may be tabulated, and a look-up (with interpolation) may be performed to find the corresponding roughness parameters.

Lighting Resolution Analysis

Before presenting some acquisition results in a section below, the effects of the discrete lighting resolution of the employed LED sphere on the specular roughness estimation may be analyzed. Given that the employed LED sphere has 20 lights around the equator, it may resolve spherical harmonic frequencies of up to order 10 in the limit (Nyquist frequency). From the frequency space analysis of Ramamoorthi and Hanrahan Ramamoorthi R., Hanrahan P.: *Frequency space environment map rendering*. Proc. of ACM SIGGRAPH '02 (2002), pp. 517-526, the number of spherical harmonic frequencies F is known to be related to the lobe width s of a Phong BRDF as $F \approx \sqrt{s}$, or to the width of a microfacet lobe as $F \approx 1/\sigma$. Given that a BRDF is defined over a hemisphere, the frequency F equals 5 in this case. Hence, $s \approx 25$, or $\sigma \approx 0.2$ may be the limit of the specular roughness (around the reflection direction) that may be resolved by such a lighting apparatus.

Alternatively, the limit of specular roughness through simulation of such discrete lighting on BRDFs may be determined with varying roughness parameters. For our simulations, a sphere may be rendered with a Ward BRDF model with spatially uniform specular roughness under the various second order spherical gradient illumination conditions as represented on the LED sphere.

Figure 5:
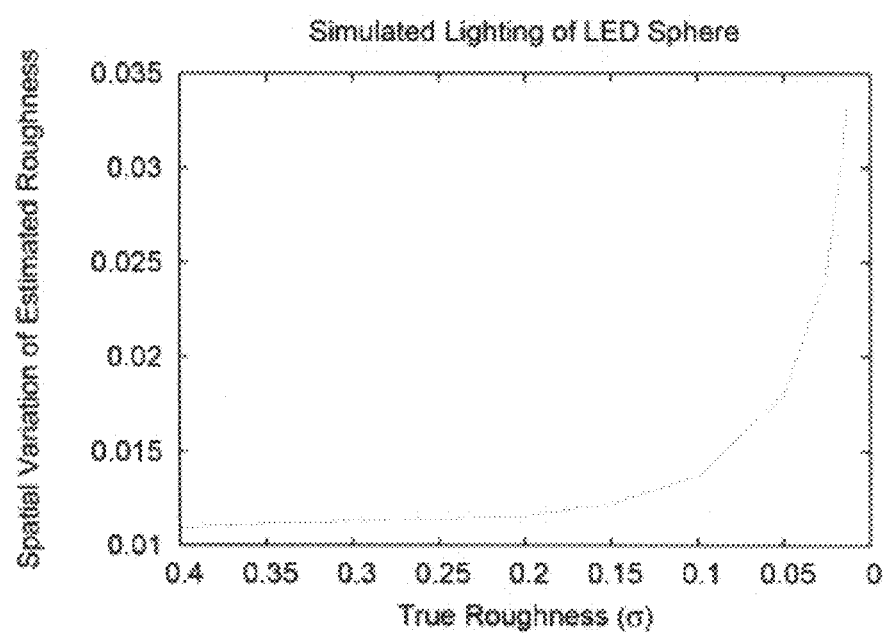
FIG. 5 illustrates spatial variation in the estimated specular roughness as a function of decreasing roughness value ($\sigma$) with the simulated discrete lighting resolution of the LED sphere with 18° light spacing.
Figure 7A:
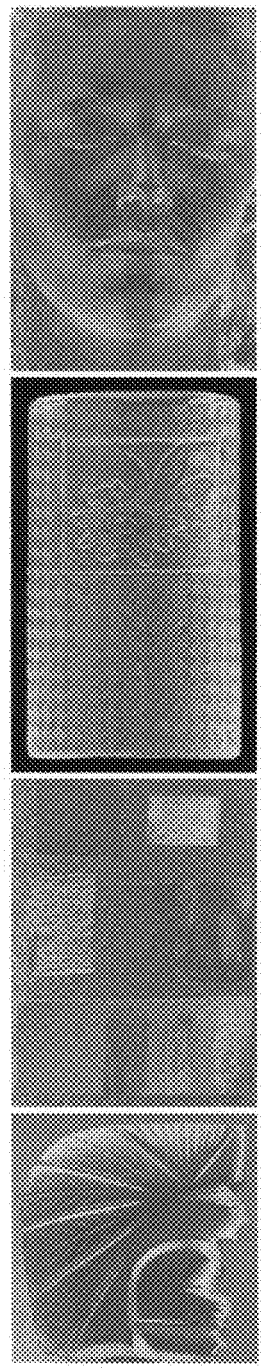
FIG. 7A-7E illustrates presents more results for various spatially varying isotropic BRDFs captured in the various measurement setups discussed above.
Figure 7B:
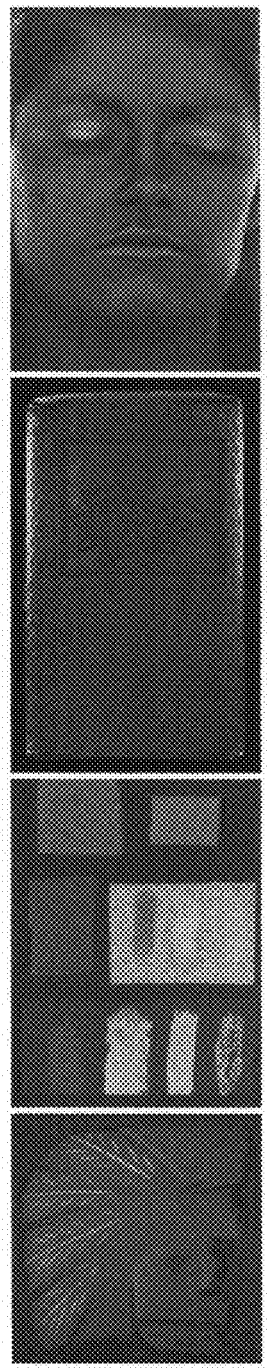
Figure 7C:
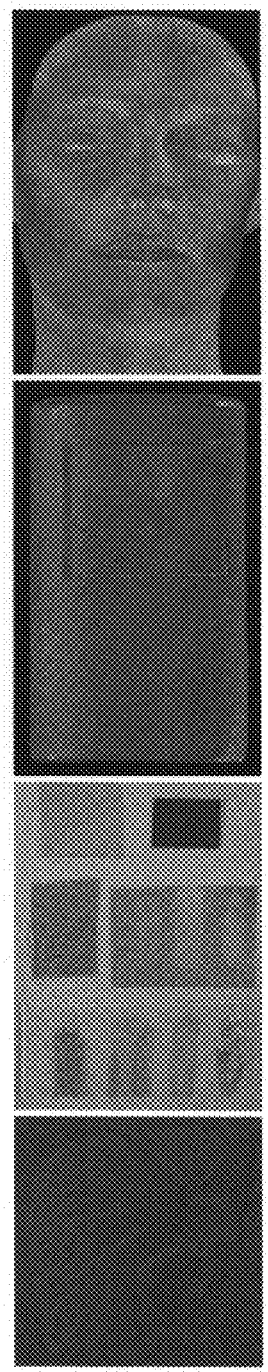
Figure 7D:
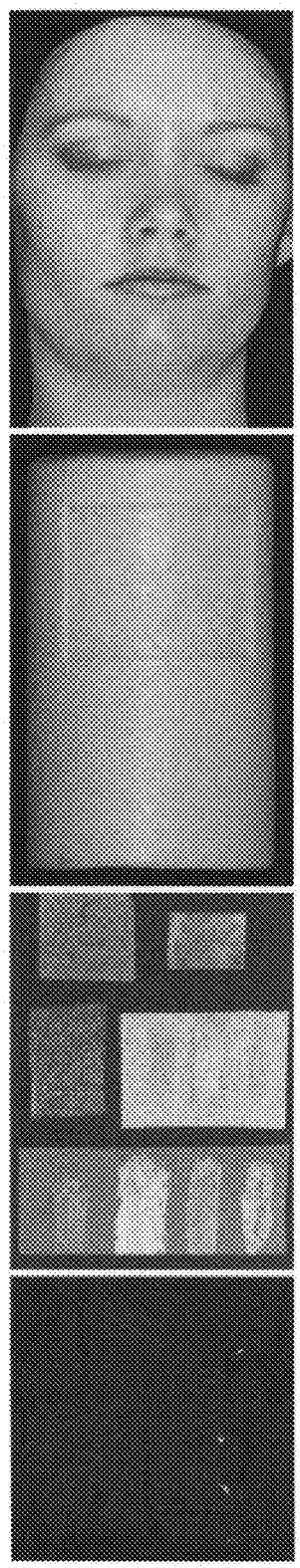
Figure 7E:
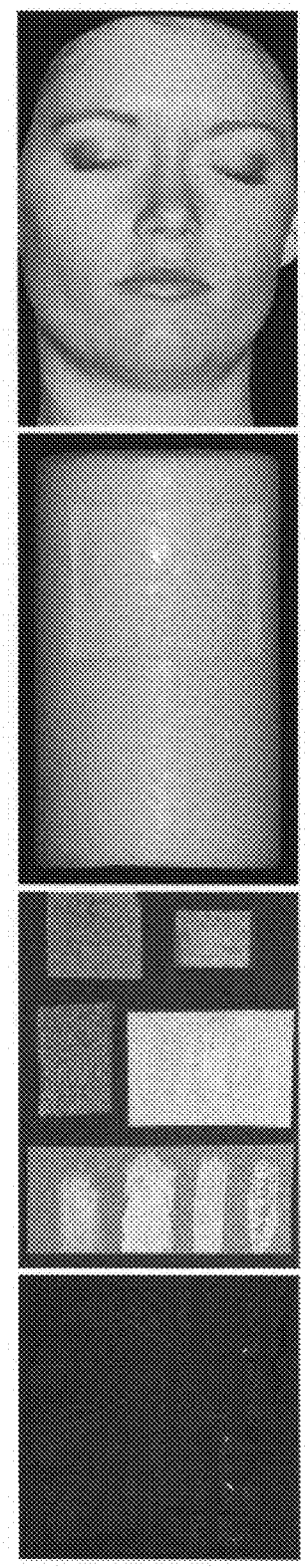

FIG. 5 illustrates spatial variation in the estimated specular roughness as a function of decreasing roughness value ($\sigma$) with the simulated discrete lighting resolution of the LED sphere with 18° light spacing. As seen, the estimate is not reliable for very specular materials. FIG. 5 presents the accuracy in terms of spatial variation in the estimated roughness under such discrete lighting. As may be seen, the estimate is stable up to a specular roughness value of around 0.2, beyond which the error in the estimate increases dramatically due to the discrete nature of the lighting. Thus, the roughness of relatively broad specular lobes with such a setup may be accurately measured.

Results and Discussion

In this section, the results of estimated spatially varying specular roughness parameters of real objects captured with second order spherical gradient illumination are presented. For anisotropic samples, the local tangent vectors may be recovered. The recovered reflectance parameters may then be used with several commonly used BRDF models to demonstrate the generality of the approach. For validation, comparisons of renderings with the estimated parameters to photographs under distant point lighting conditions are presented. Renderings may be generated using the hybrid normal map rendering technique of Ma et al. Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194.

FIG. 1 illustrates the various specular reflectance parameters recovered for an isotropic material, in this case a plastic orange, with the presented technique. The reflectance properties of the plastic orange were measured with 7 cross and parallel polarized spherical gradient illumination condition using the LED sphere setup described in Section 5.1. The image in FIG. 1D shows a rendering of the synthetic orange with the recovered specular (and diffuse) reflectance properties under a point lighting condition that is a close match to the photograph in FIG. 1E of the object under similar illumination. Here, the recovered specular roughness parameters in a Torrance-Sparrow BRDF model is employed while assuming Lambertian diffuse reflection for generating the rendering.

FIGS. 6A-6G shows results of specular reflectance parameter estimation on two anisotropic samples. The top row illustrates a red necktie. The bottom row illustrates a red satin pouch. All of the first 9 spherical harmonic illumination conditions (i.e., 0th, 1st, and 2nd order) are employed under both polarization states to recover the various specular reflectance parameters, Specular normals in FIG. 6A, Specular albedo in FIG. 6B, anisotrophy in FIG. 6C, local tangent in FIG. 6D, and bitangent vectors in FIG. 6E according to the procedure discussed above. FIG. 6F is a rendering, and FIG. 6G is a photograph. Note how the local surface and tangent orientations of such samples may be reliably estimated using only 9 illumination patterns using this technique, which can be a significant improvement over previous techniques. The recovered anisotropic reflectance parameters may be employed for the mildly anisotropic tie to a Ward BRDF model (top-row), and the Ashikhmin BRDF model for the satin pouch exhibiting significant anisotropy. The renderings of these objects with the recovered anisotropic parameters may again be a close match to the validation photographs. The main differences between the renderings and the reference photographs may be because the diffuse BRDF may most likely not be Lambertian, and that the highlights may be slightly broader due to the limited lighting resolution of the employed LED sphere.

FIG. 7 illustrates presents more results for various spatially varying isotropic BRDFs captured in the various measurement setups discussed above. These include a female subject (top-row) and a wax candle (second-row) measured in the LED sphere setup, a flat spatially varying BRDF sample measured using an LCD panel as an emitter, and a (dark) specular object, an Obsidian sculpture, measured using a reflective hemispherical dome. Specular normals are shown in FIG. 7A, specular albedos in FIG. 6B, specular roughnesses in FIG. 6C, renderings in FIG. 6D, and photographs in FIG. 6E. The recovered reflectance parameters may be applied to a Torrance-Sparrow BRDF model to generate the renderings in FIG. 6D that may be a close match to the corresponding photographs in FIG. 6E. Note that the validation photographs are under illumination from the frontal direction (top two examples) as well as from the side (bottom two examples). The spatially varying specular reflectance properties for a live subject may be reliably recovered using the technique due to the small number of required photographs, taken in just 5 seconds. The estimated roughness parameters in different regions of the face may correspond well to those reported in the literature for faces Weyrich T., Matusik W., Pfister H., Bickel B., Donner C., Tu C., McAndless J., Lee J., Ngan A., Jensen H. W., Gross M.: *Analysis of human faces using a measurement-based skin reflectance model*. ACM Transactions on Graphics 25, 3 (2006), 1013-1024.

There may be slight mismatches in the renderings with the recovered parameters and the corresponding photographs. For example, the wax candle may have a very smooth surface and its specular roughness may be slightly overestimated in some regions due to the limited lighting resolution of the LED sphere. On the other hand, some mismatches on the flat spatially varying BRDF sample (third row) may be attributed to slight inaccuracies in the estimated surface normals with the limited angular extent of the illumination from the LCD panel, and slight errors in diffuse-specular separation due the discrete sampling of the polarizer orientations in front of the camera.

As predicted from simulations, the technique may overestimate the specular roughness of a very specular object such as the Obsidian sculpture. Note that the reflective hemispherical setup may not allow for polarization based diffuse specular separation. Hence, currently, objects may be limited to those with minimal diffuse reflectance when using this setup for specular roughness estimation.

Although the second order gradient illumination conditions may have a global spherical support, occlusions may not affect the roughness and anisotropy estimation much, unlike the estimation of normals from diffuse reflections as in Ma W.-C., Hawkins T., Peers P., Chabert C.-F., Weiss M., Debevec P.: *Rapid acquisition of specular and diffuse normal maps from polarized spherical gradient illumination*. Rendering Techniques (2007), pp. 183-194. While the diffuse BRDF may have a global angular support, specular BRDFs may only have a very limited angular support. This may reduce the effects of occlusions to an (almost) binary function. Either the mirror direction may be occluded, or not. Note that even methods that rely on exhaustive sampling of all incident lighting directions may not yield reliable results when the mirror direction is occluded. For rough specular BRDFs, however, occlusions may affect the estimates. In such a case, part of the lobe may be occluded, and thus a lower variance may be reported (i.e., the estimated BRDF may be more specular).

Conclusion

In summary, higher order statistics may be used to measure the appearance properties of a spatially varying material sample. Per-surface point specular roughness and anisotropy may be accurately estimated using second order spherical gradient illumination for glossy to moderately specular materials. Limits of the technique have been demonstrated using simulations. Practical acquisition results with various measurement setups have also been demonstrated. Using this technique, a more complete material BRDF information may be obtained with fewer measurements compared to previous work.

This technique may be very useful for even traditional BRDF fitting approaches as the obtained roughness estimates may serve as the starting point for any off-line numerical optimization. The obtained roughness map may also be used to factor out the view dependent Fresnel effects from the albedo map. The BRDF may be assumed to be symmetric about the mean direction. Higher order gradients may be required to measure asymmetries such as off-specular peaks in the BRDF. The available lighting resolution may become even more critical in order to reliably measure such statistics in practice.

Cosine Lobe Based Relighting from Gradient Illumination Photographs

Figure 8:
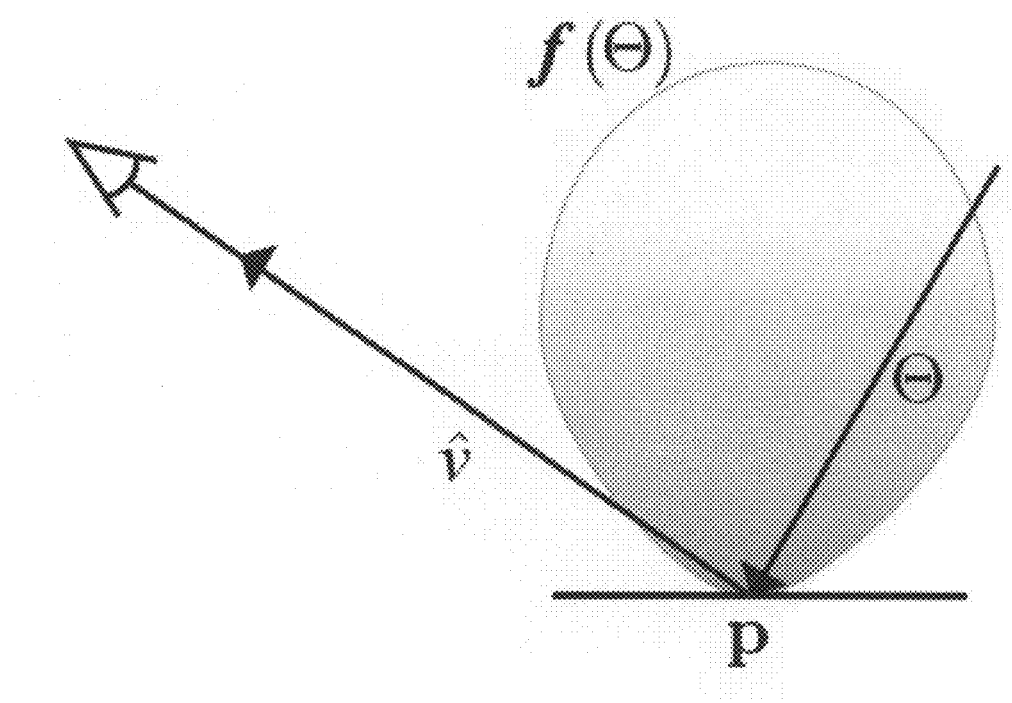
FIG. 8 is a map of incoming radiance direction on the sphere to the resulting radiance (i.e. pixel color) that is reflected towards a camera.
Figure 9A:
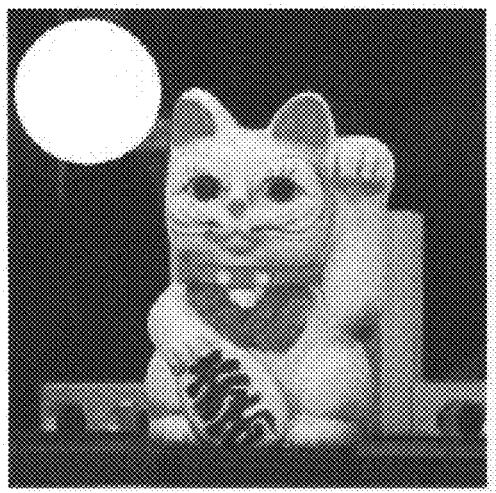
FIGS. 9A-9D illustrate a cat subject photographed under these four illumination conditions of full-on and gradient illumination.
Figure 9B:
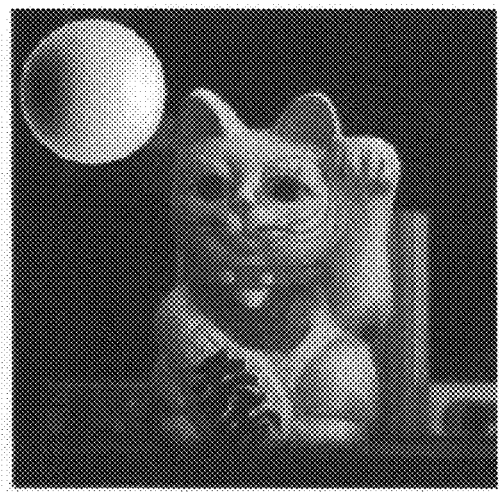
Figure 9C:
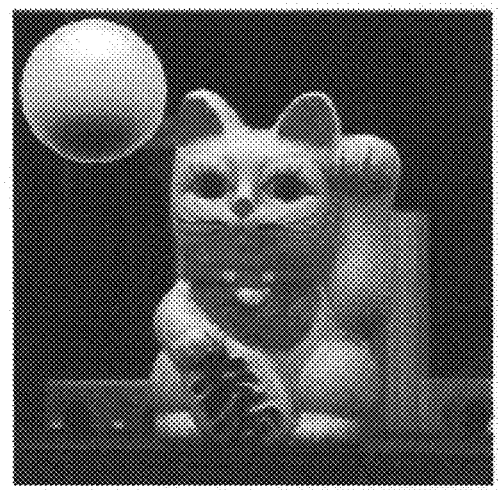
Figure 9D:
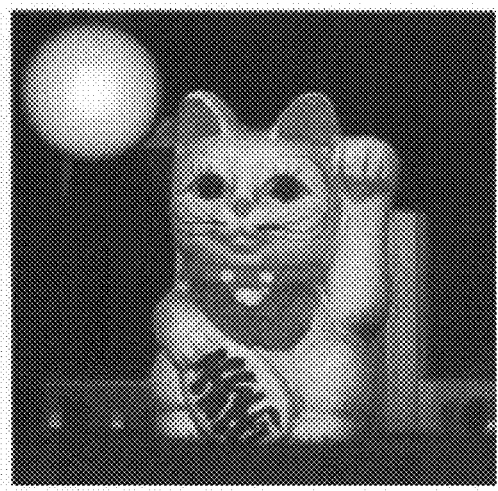

FIG. 8 is a map of incoming radiance direction on the sphere to the resulting radiance (i.e. pixel color) that is reflected towards a camera. A reflectance function $f(\Theta)$ maps incoming radiance directions $\Theta$ at a point p on a surface to the resulting radiance that is reflected along the view ray $\hat{v}$ towards a camera.

The scene inside a geodesic sphere of colored LED lights may be photographed, which may be programmed to produce gradient illumination as well as uniform white illumination, similar to Wan-Chun Ma, Tim Hawkins, Pieter Peers, Charles-Felix Chabert, Malte Weiss, and Paul Debevec, *Rapid acquisition of specular and diffuse normal maps from polarized spherical gradient illumination*, Rendering Techniques 2007: 18th Eurographics Symposium on Rendering, June 2007, pp. 183-19. Two different cosine lobe reflectance functions are explored, which may integrate easily over the uniform and gradient illumination conditions, so that an analytic fit to the observations may be obtained.

Hemispherical cosine lobes of the form $f(\Theta)=k(\hat{\alpha}\cdot\Theta)^n$ are explored for modeling diffuse and specular materials, but may be unable to represent materials with broader scattering such as fur. Alternatively, spherical cosine lobes of the form $f(\Theta)=k(\frac{1}{2}\hat{\alpha}\cdot\Theta+\frac{1}{2})^n$ are explored for broadly scattering materials, and may be still flexible enough to offer some representation of diffuse and specular materials. In both models, $\hat{\alpha}$ refers to the axis of the lobe, while k and n are constants.

Many real-world reflectance functions may be better fit by two lobes instead of one, being the so-called "diffuse" and "specular" lobes. An approximate diffuse/specular separation may be performed to recover independent diffuse and specular lobes, as well as a surface normal estimate. For offline relighting, high-frequency features may be introduced into the reflectance functions in order to produce hard cast shadows in relit images. The scene geometry may be estimated by integrating photometric normals, and then high-frequency reflectance functions may be estimated based on the visibility implied by the geometry, adjusted to maintain exact reconstruction of the input photographs. These steps are described in the sections that follow.

Data Acquisition

In the data acquisition stage, four observations $o_w$, $o_x$, $o_y$, $o_z$ may be made for each pixel and each color channel. The four observed illumination conditions defined over the unit sphere of directions $\Theta \in S^2$ with overall illumination intensity L are L, $(\frac{1}{2}\Theta_x+\frac{1}{2})L$, $(\frac{1}{2}\Theta_y+\frac{1}{2})L$, and $(\frac{1}{2}\Theta_z+\frac{1}{2})L$, corresponding to a full-on illumination condition and three orthogonal linear gradient illumination conditions.

FIGS. 9A-9D illustrate a cat subject photographed under these four illumination conditions of full-on and gradient illumination. In the case of four input photographs, the four observations may be trivially the input photograph pixel values. If a single colored gradient is used instead of separate x, y and z gradients, the observations $o_x$, $o_y$, $o_z$ may be synthesized by multiplying the full-on image with each of the three color channels of the ratio image of the colored gradient image to the full-on image. See R. J. Woodham, *Photometric method for determining surface orientation from multiple images*, Optical Engineering 19 (1980), no. 1, 139-144.

This process is illustrated in FIGS. 10A-10H. These figures illustrate a cat subject photographed under the full-on (FIG. 10A) and colored gradient (FIG. 10B) illumination conditions. FIGS. 10C-10E illustrate the red, green, and blue components of the ratio of FIG. 10B to FIG. 10A. FIGS. 10E-10H illustrate FIGS. 10C-10E multiplied by FIG. 10A.

Since the color primaries of the LEDs may not be exactly the same as the color primaries of the camera sensors, a color correction matrix may be calibrated prior to acquisition in order to reduce cross-talk between color channels.

Cosine Lobe Reflectance Functions

It may be helpful to examine the general case of the integral of a hemispherical cosine lobe $k(\hat{\alpha}\cdot\Theta)^n$ times an arbitrary linear gradient $\beta\cdot\Theta+b$ ($\beta$ not necessarily unit) over the hemisphere $\Omega_+(\hat{\alpha})$ of directions on the positive side of the axis of the lobe, which has the closed form:

$$\int_{\Omega+(\hat{\alpha})} k(\hat{\alpha}\cdot\Theta)^n (\beta\cdot\Theta + b) d\omega_\Theta = \frac{2\pi k(\hat{\alpha}\cdot\beta)}{n+2} + \frac{2\pi kb}{n+1}. \quad (10)$$

From here, the four illumination condition observations may be derived:

$$\int_{\Omega+(\hat{\alpha})} k(\hat{\alpha}\cdot\Theta)^n L d w_\Theta = \frac{2\pi kL}{n+1}, \quad (11)$$

$$\int_{\Omega+(\hat{\alpha})} k(\hat{\alpha}\cdot\Theta)^n \left(\frac{1}{2}\Theta_x + \frac{1}{2}\right) L d w_\Theta = \frac{\pi kL\hat{\alpha}_x}{n+2} + \frac{\pi kL}{n+1}, \quad (12)$$

$$\int_{\Omega+(\hat{\alpha})} k(\hat{\alpha}\cdot\Theta)^n \left(\frac{1}{2}\Theta_y + \frac{1}{2}\right) L d w_\Theta = \frac{\pi kL\hat{\alpha}_y}{n+2} + \frac{\pi kL}{n+1},$$

$$\int_{\Omega+(\hat{\alpha})} k(\hat{\alpha}\cdot\Theta)^n \left(\frac{1}{2}\Theta_z + \frac{1}{2}\right) L d w_\Theta = \frac{\pi kL\hat{\alpha}_z}{n+2} + \frac{\pi kL}{n+1}.$$

Substituting the four observations $o_w$, $o_x$, $o_y$, $o_z$ corresponding to the four lighting conditions and requiring $\hat{\alpha}$ to be a unit vector yields a system of five equations:

$$o_w = \frac{2\pi kL}{n+1}, \quad (13)$$

$$o_x = \frac{\pi kL\hat{\alpha}_x}{n+2} + \frac{\pi kL}{n+1},$$

$$o_y = \frac{\pi kL\hat{\alpha}_y}{n+2} + \frac{\pi kL}{n+1},$$

$$o_z = \frac{\pi kL\hat{\alpha}_z}{n+2} + \frac{\pi kL}{n+1},$$

$$\|\hat{\alpha}\| = 1.$$

These equations may admit a single closed-form solution for the cosine lobe:

$$\hat{\alpha} = \frac{\alpha}{\|\alpha\|}, \quad (14)$$

$$n = \frac{2\|\alpha\| - o_w}{o_w - \|\alpha\|},$$

$$k = \frac{o_w(n+1)}{2\pi L}.$$

where $\alpha = \langle 2o_x - o_w, 2o_y - o_w, 2o_z - o_w \rangle$.

Note that the cosine lobe axis may be obtained from the gradient illumination condition observations in a manner similar to the method in Wan-Chun Ma, Tim Hawkins, Pieter Peers, Charles-Felix Chabert, Malte Weiss, and Paul Debevec, *Rapid acquisition of specular and diffuse normal maps from polarized spherical gradient illumination*, Rendering Techniques 2007: 18th Eurographics Symposium on Rendering, June 2007, pp. 183-19 for obtaining the mean spherical angle of a reflectance function. This may be due to the symmetry of the cosine lobe reflectance function about its axis.

It may be shown by a similar argument that a spherical cosine lobe of the form $k(\frac{1}{2}\hat{\alpha}\cdot\Theta + \frac{1}{2})^n$ has the solution:

$$\hat{\alpha} = \frac{\alpha}{\|\alpha\|}, \quad (15)$$

$$n = \frac{2\|\alpha\|}{o_w - \|\alpha\|},$$

$$k = \frac{o_w(n+1)}{4\pi L}.$$

where $\alpha = \langle 2o_x - o_w, 2o_y - o_w, 2o_z - o_w \rangle$.

Figure 11A:
FIGS. 11A-11F illustrate coefficients for the cat subject under the hemispherical cosine lobe model.
Figure 11B:
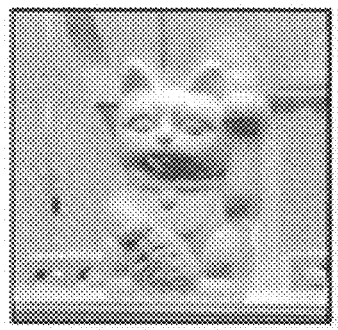
Figure 11C:
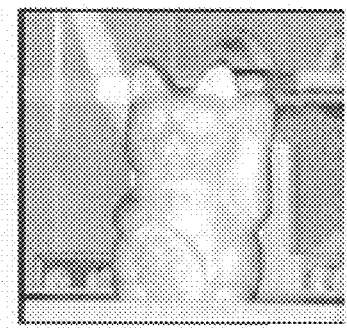
Figure 11D:
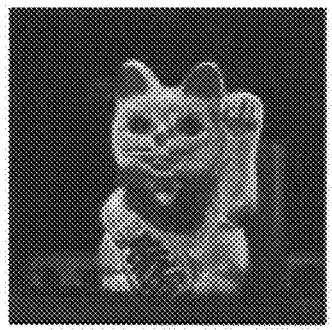
Figure 11E:
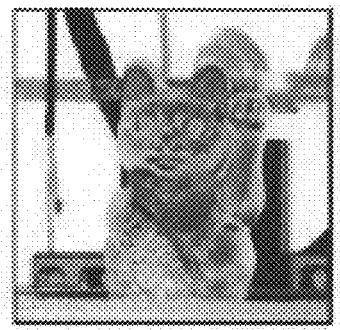
Figure 11F:

FIGS. 11A-11F illustrate coefficients for the cat subject under the hemispherical cosine lobe model. FIGS. 11A-11C illustrate from left to right $\hat{\alpha}_x$, $\hat{\alpha}_y$, $\hat{\alpha}_z$. FIGS. 11D-11F illustrate from left to right k, n, zoom of n. The value of the exponent n in the figure is scaled by one eighth.

Only the coefficients of the cosine lobe reflectance model may be stored at each pixel for each color channel.

FIGS. 11A-11F visualize the coefficients for a cat subject, where the red, green, and blue channel coefficients are grouped and displayed as color images. Once the cosine lobes for each pixel and each color channel are computed, relit images may be synthesized for any distant illumination condition. Relit images may be computed simply by sampling the cosine lobe reflectance functions for each light source in the novel illumination condition.

Figure 12A:
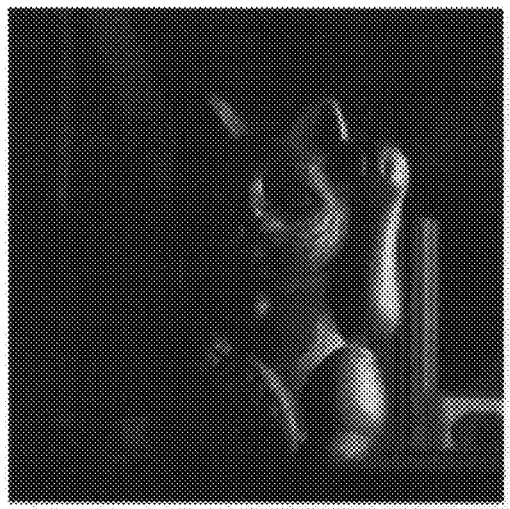
FIGS. 12A-12D illustrate examples of relit images generated under a novel point-light illumination condition.
Figure 12B:
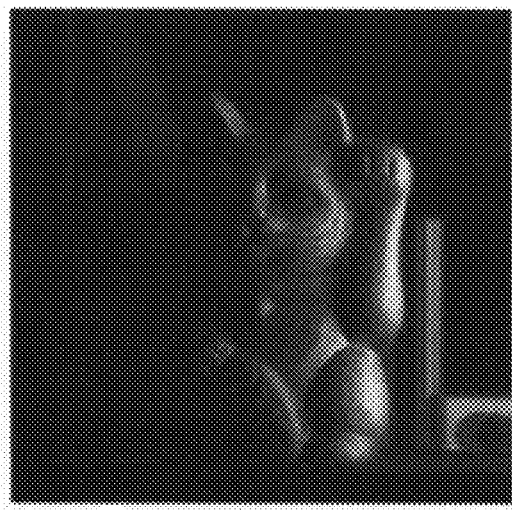
Figure 12C:
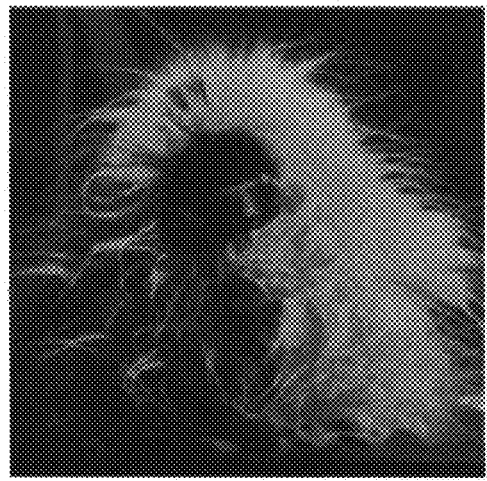
Figure 12D:
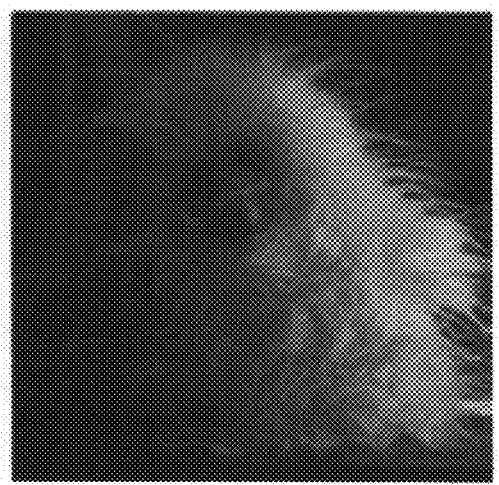

FIGS. 12A-12D illustrate examples of relit images generated under a novel point-light illumination condition. The light is coming from far right. FIGS. 12A and 12C are the hemispherical cosine lobe model. FIGS. 12B and 12D are the spherical cosine lobe model.

Diffuse/Specular Separation

The four observations under different illumination conditions in general may not contain enough information to be separated into diffuse and specular components. However, under certain assumptions about isotropy and the breadth of the diffuse and specular lobes, a separation may indeed be obtained. Notably, other than the assumptions just mentioned, this separation may not depend on any other assumptions about the shape of the lobes, so it may find applications beyond cosine lobe reflectance models.

The observations o may be presumed to be a sum of diffuse and specular components d and s:

$$o = d + s. \quad (16)$$

For each color channel, a quantity g may describe the gradient illumination observations normalized by the full-on illumination observation:

$$g = \frac{1}{o_w}\langle 2o_x - o_w, 2o_y - o_w, 2o_z - o_w \rangle. \quad (17)$$

Quantities d and s may describe the normalized diffuse and specular components:

$$d = \frac{1}{d_w}\langle 2d_x - d_w, 2d_y - d_w, 2d_z - d_w\rangle;$$ (18)

$$s = \frac{1}{s_w}\langle 2s_x - s_w, 2s_y - s_w, 2s_z - s_w\rangle.$$

It follows that:

$$g = \frac{d_w}{d_w + s_w}d + \frac{s_w}{d_w + s_w}s.$$ (19)

and hence g may lie on the line segment $\overline{ds}$.

If the reflectance is assumed to be isotropic, and that the diffuse component d is aligned with the surface normal n, then the vector v may point towards the viewer and the vectors g, d and s may all lie in the same plane. Hence, a coordinate system may be defined in the plane defined by v and (mean) g, and only two-dimensional vectors may be considered from here on by projecting onto this plane. On this plane, the angle Θ between v and n may be equal to the angle between n and the ideal reflection vector r.

Figure 13:
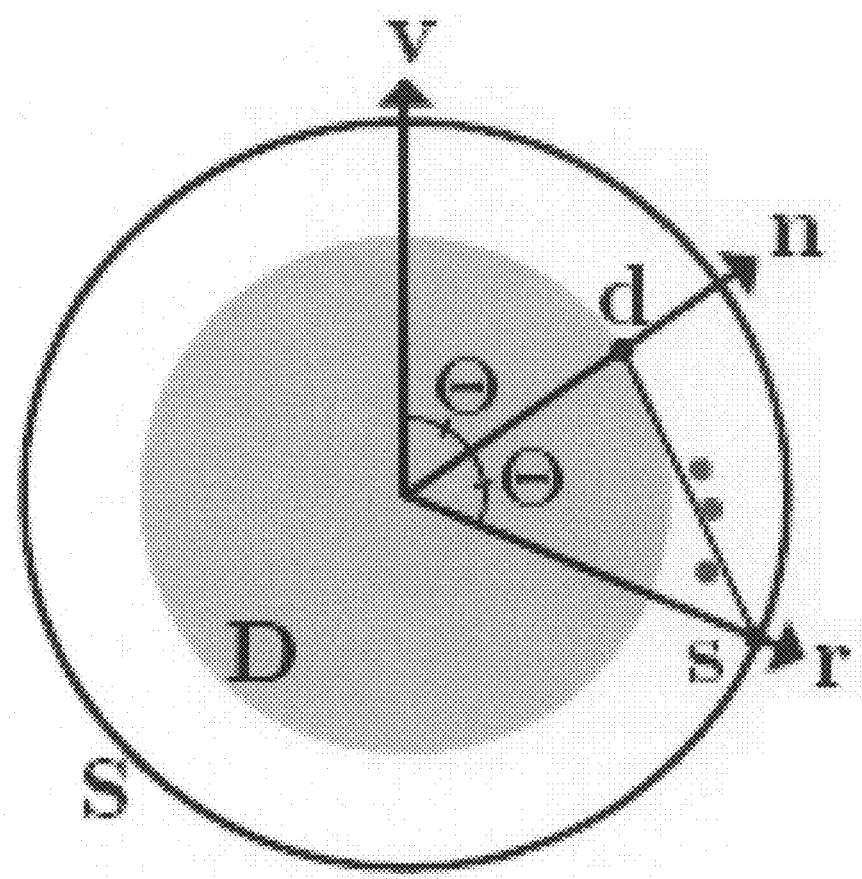
FIG. 13 illustrates on the plane defined by the view vector v and the (mean) measured vector g.

FIG. 13 illustrates on the plane defined by the view vector v and the (mean) measured vector g. The red, green, and blue dots are the normalized gradient vectors g of the red, green and blue color channels; n is the surface normal; r is the ideal reflection vector; d and s are the normalized diffuse and specular components; and D and S are circles of length |d| and |s|. If |d| and |s| are known, then Θ is uniquely determined as the angle that yields the best fit for the line segment $\overline{ds}$ to the vectors g. FIG. 13 depicts the geometric relationships between all of these vectors. d is the intersection of n with a circle of radius |d|, and s is the intersection of r with a circle of radius |s|.

If |d| and |s| are known, but n and r are unknown, then n and r (and hence d and s) may be recovered by finding the angle Θ that yields the best fit for the line segment $\overline{ds}$ to the vectors g of each color component. For example, by Eq. (14) it may be shown that |d|=⅔ for ideal Lambertian (diffuse) reflectance, and |s|=1 for ideal specular (perfect mirror) reflectance. The normalized shape of the lobes may be assumed to be wavelength-independent (though the intensity of the lobes may still be wavelength-dependent), so just one Θ is found to explain all three color channels. As the behavior of the line segment $\overline{ds}$ is non-linear, no closed form for Θ could be obtained and hence a simple line search may be sued to find it.

After Θ is found, the vectors g of each color channel may be projected onto the line segment $\overline{ds}$ to compute the (per-color-channel) quantity $$\frac{s_w}{d_w + s_w},$$

which allows the un-normalized diffuse and specular components d and s to be recovered. However, since the data may deviate from the assumptions in several respects, the vectors g may not lie exactly on the line segment $\overline{ds}$, and therefore the reconstruction of the data using d and s may not be exact. Therefore, let d=g−s, which has the effect of lumping the residuals of the reconstruction into the diffuse component, which seems acceptable as occlusion and interreflection already pollute the diffuse component to some degree.

Finally, with the recovered diffuse and specular components d and s for each illumination condition, independent diffuse cosine lobes and specular cosine lobes may be fit. By this construction, the diffuse and specular cosine lobes reconstruct the input observations exactly.

Figure 14A:
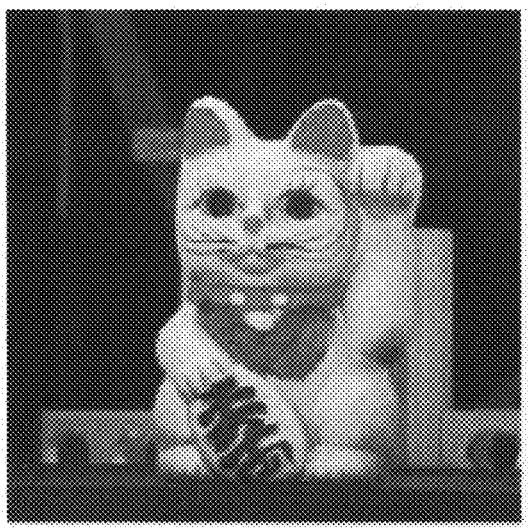
FIGS. 14A-14D illustrate diffuse/specular separation of the cat subject.
Figure 14B:
Figure 14C:
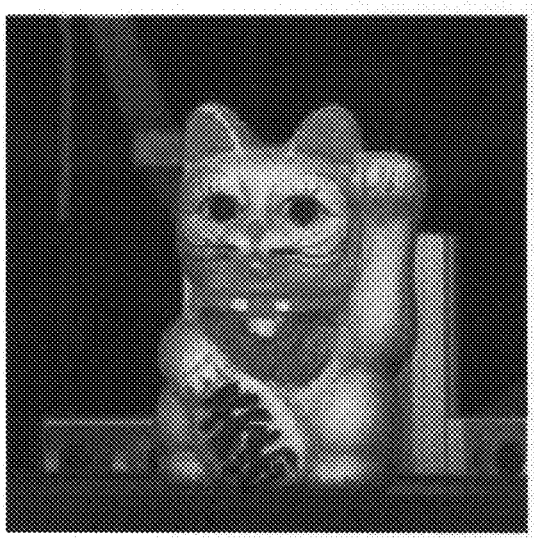
Figure 14D:
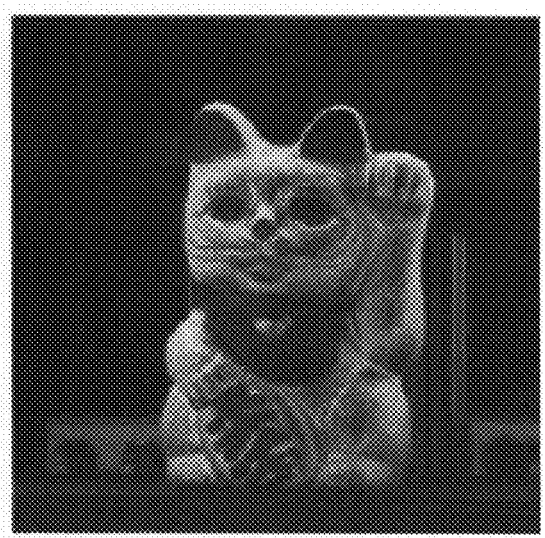

FIGS. 14A-14D illustrate diffuse/specular separation of the cat subject. FIG. 14A illustrates original full-on illumination photograph, FIG. 14B illustrates recovered normals; FIG. 14C illustrates recovered diffuse component; and FIG. 14D illustrates recovered specular component. These figures are an example of diffuse/specular separation under the Lambertian/ideal specular assumption.

Estimating Geometry and Shadows

The cosine lobe reflectance function $f(\Theta)$ estimated by this method may have only low-frequency features. Thus, while the low-frequency illumination condition input photographs are reconstructed exactly, hard cast shadows cannot be synthesized for novel illumination conditions having high-frequency features. To enable the computation of hard cast shadows in the relit images, scene geometry may be estimated by integrating the surface normals estimated in the diffuse/specular separation phase. Integration may proceed using a method similar to Berthold K. P. Horn and Michael J. Brooks, *The variational approach to shape from shading*, vol. 33, 1986, pp. 174-208.

Figure 15A:
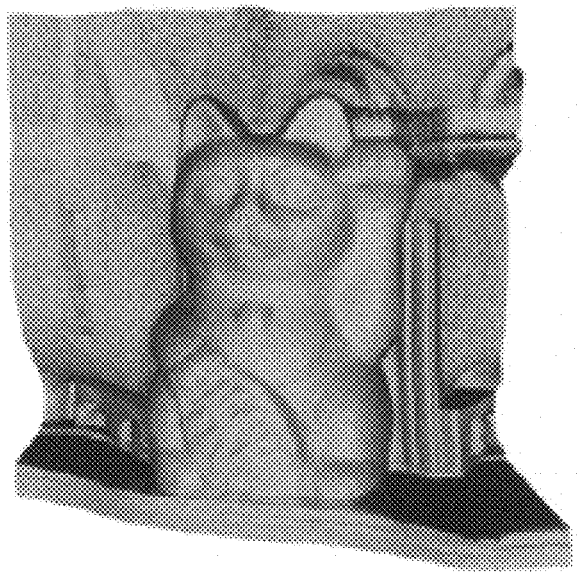
FIGS. 15A-15D illustrate reconstructed geometry from photometric normals.
Figure 15B:
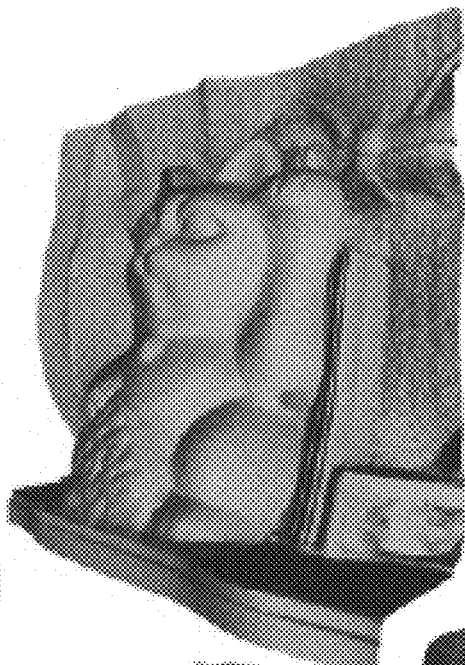
Figure 15C:
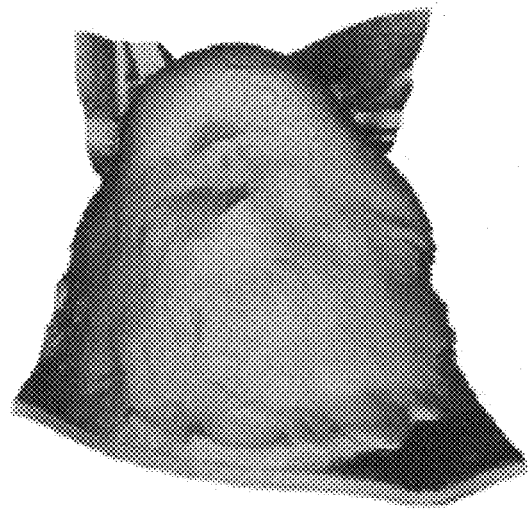
Figure 15D:
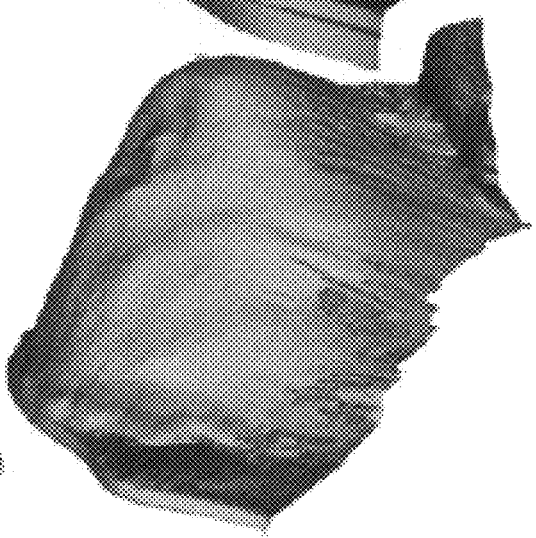

FIGS. 15A-15D illustrate reconstructed geometry from photometric normals. FIGS. 15A and 15D illustrate two views of the cat subject. FIGS. 15C and 15D illustrate two views of the duck subject.

Figures 16A, 16B:
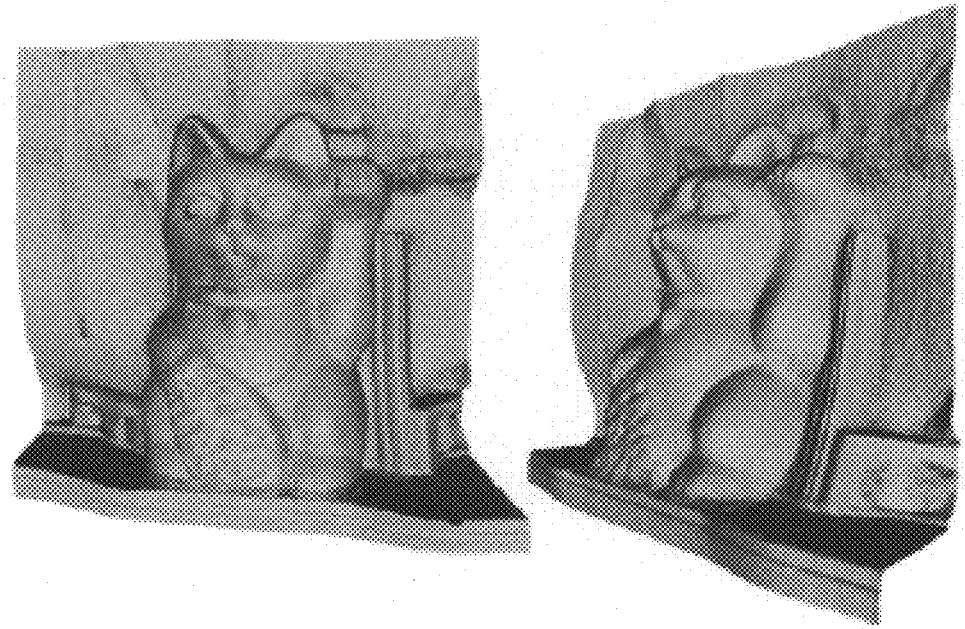
FIGS. 16A and 16B illustrate reconstructed geometry for the cat subject, with normals derived from two photos instead of four.

FIGS. 16A and 16B illustrate reconstructed geometry for the cat subject, with normals derived from two photos instead of four.

Once the scene geometry has been estimated, an adjusted reflectance function $f'(\Theta)$ may be computed that exhibits hard shadows cast by the geometry. First, consider a reflectance function $f^*(\Theta)$ adjusted simply by occluding any light directions that hit scene geometry:

$$f^*(\Theta) = f(\Theta)\text{visible}(\Theta),$$ (20)

where visible (Θ) is 0 if the direction Θ is occluded by geometry or outside of the domain of $f(\Theta)$, and 1 otherwise. To reduce shadow aliasing, visible (Θ) may be allowed to fall off gradually from 1 to 0 near the surface of the geometry, so that a ray that just grazes the geometry will be attenuated, but still continue through the scene.

In general, relighting using $f^*(\Theta)$ may not reconstruct the input photographs exactly, since the low-frequency component of the reflectance function may generally be altered by the visibility masking. To correct this, a scaling factor s may be introduced to restore the overall reflectance magnitude, and a low-frequency "ambient" term p·Θ may be introduced to restore the original low-frequency component of the reflectance function:

$$f'(\Theta) = sf^*(\Theta) + p\cdot\Theta.$$ (21)

Let $o^*_w$, $o^*_x$, $o^*_z$ represent the synthesized observations using $f^*(\Theta)$, computed by numerical integration:

$$o^*_w = \int_{S^2} f^*(\Theta) L d w_\Theta,$$ (22)

$$o^*_x = \int_{S^2} f^*(\Theta)\left(\frac{1}{2}\Theta_x + \frac{1}{2}\right) L d w_\Theta,$$

-continued $$o_y^* = \int_{S^2} f^*(\Theta)\left(\frac{1}{2}\Theta_y + \frac{1}{2}\right)Ld\omega_\Theta,$$

$$o_z^* = \int_{S^2} f^*(\Theta)\left(\frac{1}{2}\Theta_z + \frac{1}{2}\right)Ld\omega_\Theta.$$

Then the observations are corrected:

$$o_w = so_w^* + \int_{S^2} (p \cdot \Theta)Ld\omega_\Theta, \quad (23)$$

$$o_x = so_x^* + \int_{S^2} (p \cdot \Theta)\left(\frac{1}{2}\Theta_x + \frac{1}{2}\right)Ld\omega_\Theta.$$

$$o_y = so_y^* + \int_{S^2} (p \cdot \Theta)\left(\frac{1}{2}\Theta_y + \frac{1}{2}\right)Ld\omega_\Theta,$$

which admit one closed-form solution:

$$o_z = so_z^* + \int_{S^2} (p \cdot \Theta)\left(\frac{1}{2}\Theta_z + \frac{1}{2}\right)Ld\omega_\Theta. \quad (24)$$

Figure 17:
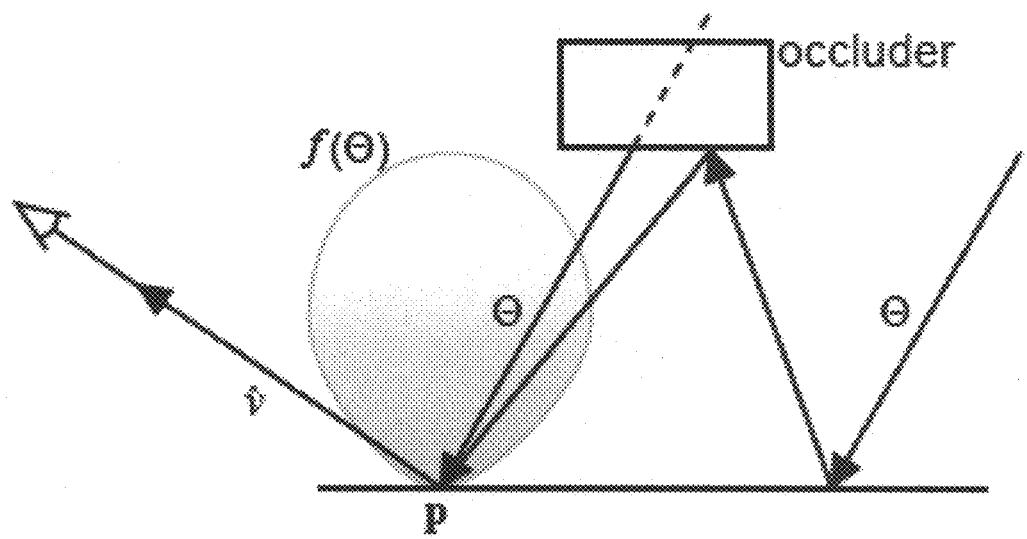
FIG. 17 illustrates how, if a ray cast in the direction hits scene geometry, then the only way $\Theta$ may contribute to the resulting radiance is by indirect bounce light.

FIG. 17 illustrates how, if a ray cast in the direction hits scene geometry, then the only way Θ may contribute to the resulting radiance is by indirect bounce light.

The plausibility of the low-frequency term p·Θ may be justified as follows: If a ray cast in the direction Θ hits scene geometry, then the only way Θ may contribute to the resulting radiance may be by indirect bounce light, as illustrated in FIG. 17. Indirect bounce light is often low-frequency in nature, so it seems appropriate to model it by a low-frequency term.

Relighting may now proceed by sampling ƒ'(Θ) for each light. To avoid storing the entire function ƒ'(Θ) at each pixel, instead store the scene geometry as a depth map, the original estimated reflectance function ƒ(Θ), and the correction coefficients s and p, and use ray casting to evaluate visible (Θ) as needed. Errors in the scene geometry, especially in the background plane, may introduce unwanted shadows into the relit images. To reduce this problem at the expense of some manual intervention, introduce a user-supplied binary mask to prevent the background elements from occluding the foreground elements.

FIGS. 18A-18E illustrate how a user-supplied visibility mask (center) reduces unwanted shadows. FIGS. 18 and 18D illustrate relit images under two point-light illumination conditions, no mask supplied. FIGS. 18C and 18E illustrate mask supplied. FIG. 18B shows such a mask, and compares the results obtained with and without using the mask.

Conclusions

FIG. 19 illustrates that the visibility masking assumption does not hold for highly scattering materials such as the duck subject, resulting in an inappropriately hard shadow terminator.

Figure 20:
FIG. 20 illustrates relit images of cat subject under novel point light illumination conditions.

FIG. 20 illustrates relit images of cat subject under novel point light illumination conditions. Row A illustrates linear basis using four photographs. Row B illustrates hemispherical cosine lobe using two photographs. Row C illustrates hemispherical cosine lobe using four photographs. Row D illustrates diffuse and specular hemispherical cosine lobes using four photographs. Row E illustrates diffuse and specular hemispherical cosine lobes with hard cast shadows, using four photographs and user-supplied visibility mask. Row F illustrates ground truth, with inset gray balls indicating illumination direction.

Figure 21:
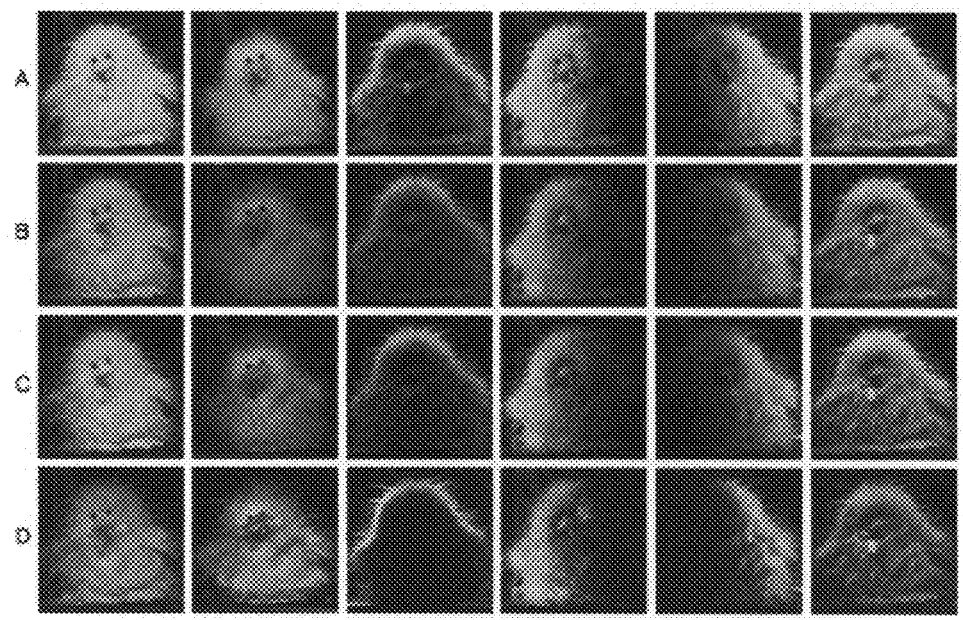
FIG. 21 illustrates relit images of duck subject under novel point light illumination conditions.

FIG. 21 illustrates relit images of duck subject under novel point light illumination conditions. Row A illustrates linear basis using four photographs. Row A illustrates spherical cosine lobes using two photographs. Row A illustrates spherical cosine lobes using four photographs. Row D illustrates ground truth.

FIG. 20 and FIG. 21 thus illustrate ground-truth comparisons with several relighting methods on the cat and duck subject, respectively. For both subjects, a linear basis relighting method is included as a baseline, which attempts to synthesize novel illumination conditions as a linear combination of the four observed gradient conditions. Note that all relighting methods tested here, including the linear basis method, reconstruct the set of input photographs exactly.

The cat subject relit with the linear basis reference method appears flat and does not convey the shape of the cat well. The two-photograph hemispherical cosine lobe method has noticeably lower quality than the four-photograph hemispherical cosine lobe method, but could be suitable for applications with limited capture budget such as video relighting. Separating the reflectance into diffuse and specular lobes significantly may improve the result for the cat: the behavior of the materials under back-lighting is plausible, and specular highlights are more pronounced. Notably, the diffuse/specular separation visualized in FIG. 14 largely agrees with the materials of the actual subject. For example, the golden body of the cat is a specular material with dependency on angle, in this case a gold paint. The red collar, ears, and nose have a dominant diffuse red component with a small specular component in all channels, in this case a semi-gloss red paint. The green bib has a dominant diffuse green component, in this case a very soft diffuse green paint with a faint gloss. Most notable is the visual softness of the materials in the diffuse component. Almost without exception, the specular highlights in the original photograph are separated into the specular component, leaving a smooth diffuse component. The most visible examples include the flecks of glitter on the green bib, and the highlights in the eyes. The reconstructed geometry clearly suffers from depth ambiguities in the normal integration, but in a relighting scheme that does not attempt to alter the viewpoint, the hard cast shadows and self shadowing appear to be convincing in most cases. However, the requirement of a user-supplied visibility mask to avoid unwanted shadows in some of the lighting conditions is a notable limitation of the method, and future work should attempt to generate such masks automatically, or to improve the geometry estimate to remove the need for such masks.

The duck subject relit with the linear basis reference method performs better than on the cat, but does exhibit some disturbing shadowing artifacts. The two-photograph and four-photograph spherical cosine lobe reconstructions of the duck both reproduce the scattering of the fur well in most places, and still provide a good approximation of the other materials in the scene, including the specular necktie, but some lack of self shadowing is evident. Hard cast shadows for the duck fail altogether, as shown in FIG. 14, because the visibility masking assumption does not hold for highly scattering materials. Better self-shadowing across a wider range of materials would be an improvement sought after in future work, perhaps using a more complete estimate of visibility based on the reflectance function estimates of all pixels.

Ground truth comparisons reveal several limitations with this method, but even with these limitations the method produces visually plausible results over a wide range of materials and illumination using very few input observations. Furthermore, the results may be more consistent with ground truth than those obtained from using the same input photographs as a linear basis.

Figure 22:
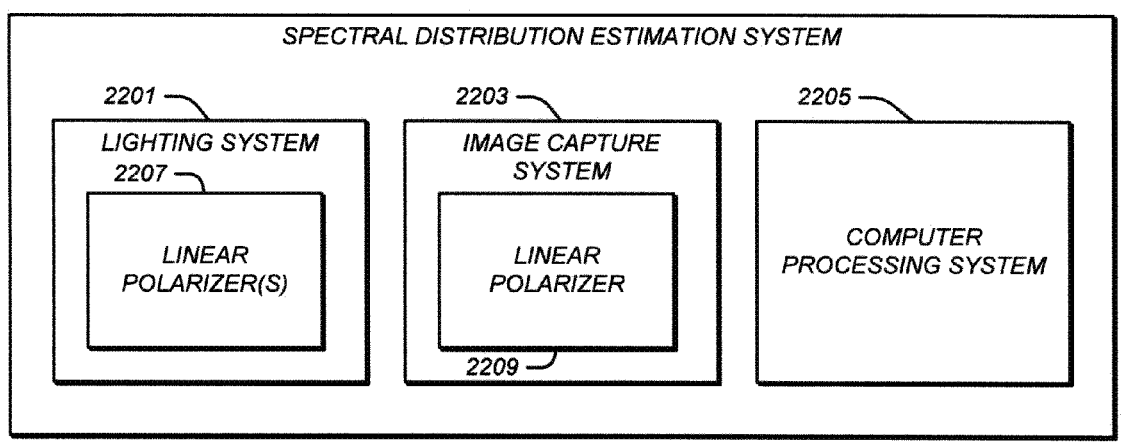
FIG. 22 illustrates a spectral distribution estimation system.

FIG. 22 illustrates a spectral distribution estimation system. This system may be used to estimate the surface roughness, tangent vectors, and other spectral parameters of points on a surface of an object.

The spectral distribution estimation system may include a lighting system 2201, an image capture system, 2203, and a computer processing system 2205.

The lighting system 2201 may be configured to generate any or all of the lighting patterns discussed above. The lighting system 2201 may include a plurality of light sources. The light sources may be the pixels on an LCD display, such as a flat LCD display, or may be pinpoint light sources, such as LEDs. The pinpoint light sources, such as LEDs, may be arranged in a flat two-dimensional array or in a three-dimensional array, such as a curved three-dimensional array. The curved array may be hemispherical or spherical, such as a spherical array of LEDs, as illustrated in FIG. 3 of U.S. Pat. No. 7,744,613, the entire contents of this patent being incorporated herein by reference.

The lighting system 2201 may include a controller configured to adjust the intensity of the various light sources so as to cause them to generate any or all of the light patterns discussed above. The light sources and/or the controller may be configured to cause the generated light from each light source to be white light or, in a different embodiment, light of one or more colors.

The lighting system 2201 may include linear polarizers 2207. Each of the linear polarizers 2207 may be configured to linearly polarize the light emanating from one of the light sources. When the light sources are pinpoint light sources, for example, a linear polarizer may be positioned so as to linearly polarize the light from each pinpoint light source.

The image capture system 2203 may be configured to capture an image of a surface of the object when illuminated by the different illumination patterns discussed above, each at a different time. The image capture system 2203 may include a camera, such as a digital camera. A linear polarizer 2209 may be positioned so as to linearly polarize the light reflected from a surface of the object before it is captured by the image capture system 2203. The linear polarizer 2209 may be configured so that it can be adjusted either by manual or automated means, so as to adjust the direction of the linear polarization. For example, the linear polarizer 2209 may be configured so that it can adjust the linear polarization by approximately 90°. Each illumination pattern may be captured by the image capture system 2203 with the linear polarizer 2209 in a first position and then again in a second position which alters the linear polarization from the first position by approximately 90°.

The computer processing system 2205 may be configured to receive each of the images captured by the image capture system 2203 and to compute an estimate of the spectral distribution of each point on a surface of the object based on these images. This may include a computation of the specular roughness and the tangent vectors for each point on a surface of the object. The computer processing system 2205 may be configured to make these computations in accordance with one or more of the equations, principles, and algorithms discussed above.

The computer processing system 2205 may include computer hardware and associate computer software configured to make these computations based on these equations, principles, and algorithms. The software may include code compiled with software development tools such as Microsoft Visual Studio, scripting software such as Python for controlling the hardware components, and/or a plug-in to mathematical processing software such as Matlab Toolbox. The computer processing system 2205 may include a field programmable gate array unit configured to make all or part of the computations. The computer software may be contained on non-transitory, computer readable storage media in the form of computer-readable instructions which, when executed by the computer processing system 2205, cause it to make the computations discussed herein.

The components, steps, features, objects, benefits and advantages which have been discussed are merely illustrative. None of them, nor the discussions relating to them, are intended to limit the scope of protection in any way. Numerous other embodiments are also contemplated. These, include embodiments which have fewer, additional, and/or different components, steps, features, objects, benefits and advantages. These also include embodiments in which the components and/or steps are arranged and/or ordered differently.

For example, there may be more cameras, more lighting components, and/or video projectors for capturing additional information alongside the information described above. Some embodiments may omit polarization filters or may use a different configuration of polarization filters, so that the method may be applied to views from multiple cameras. Images may be captured under more illumination patterns, in addition to the illumination patterns described above. The lighting system may include extended light sources, or freeform sampling of illumination directions. for example, using hand-held lights.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials which have been described and their equivalents. Similarly, the phrase "step for" when used in a claim is intended to and should be interpreted to embrace the corresponding acts which have been described and their equivalents. The absence of these phrases in a claim mean that the claim is not intended to and should not be interpreted to be limited to any of the corresponding structures, materials, or acts or to their equivalents.

Nothing which has been stated or illustrated is intended or should be interpreted to cause a dedication of any component, step, feature, object, benefit, advantage, or equivalent to the public, regardless of whether it is recited in the claims.

The scope of protection is limited solely by the claims which now follow. That scope is intended and should be interpreted to be as broad as is consistent with the ordinary meaning of the language which is used in the claims when interpreted in light of this specification and the prosecution history which follows and to encompass all structural and functional equivalents.

The invention claimed is:

1. A system for estimating the specular roughness of points on a surface of an object comprising:
    a lighting system configured to illuminate the surface of the object at different times with different illumination patterns, each illumination pattern illuminating the surface from a plurality of different directions and forming an intensity gradient having an order of no more than two;

an image capture system configured to capture an image of the surface of the object when illuminated by each of the different illumination patterns at each of the different times; and a computer processing system configured to compute the specular roughness of each point on the surface of the object based on the images captured by the image capture system.

2. The system of claim 1 wherein:

the lighting system is configured such that some of the illumination patterns have an intensity gradient having an order of two; and the computer processing system is configured to compute the specular roughness of each point on the surface of the object based on the images captured by the image capture system while the surface is illuminated by the illumination patterns which have an intensity gradient having an order of two.

3. The system of claim 2 wherein the lighting system includes a linear polarizer configured to linearly polarize the illumination patterns that have an intensity gradient having an order of two.

4. The system of claim 3 wherein the image capture system includes a linear polarizer configured to linearly polarize the images of the surface of the object.

5. The system of claim 4 wherein the linear polarizer is configured to be user-adjustable so as to controllably change the direction of the polarization of the images of the surface of the object.

6. The system of claim 2 wherein the surface of the object is substantially isotropic and wherein:

the lighting system is configured such that three of the illumination patterns have an order of two; and the computer processing system is configured to compute the specular roughness of each point on the surface of the object based on the images captured by the image capture system under the illumination of only three illumination patterns having an order of two.

7. The system of claim 6 wherein:

the lighting system is configured such that four of the illumination patterns have an order of one; and the computer processing system is configured to compute the specular roughness of each point on the surface of the object based on the images captured by the image capture system under the illumination of only four illumination patterns having an order of one.

8. The system of claim 2 wherein the surface of the object is substantially anisotropic and wherein:

the lighting system is configured such that five of the illumination patters have an order of two; and the computer processing system is configured to compute the specular roughness and a tangent vector of each point on the surface of the object based on the images captured by the image capture system under the illumination of only five illumination patterns having an order of two.

9. The system of claim 8 wherein:

the lighting system is configured such that four of the illumination patters have an order of one; and the computer processing system is configured to compute the specular roughness and the tangent vector of each point on the surface of the object based on the images captured by the image capture system under the illumination of only four illumination patterns having an order of one.

10. The system of claim 2 wherein the lighting system includes a substantially flat LCD display.

11. The system of claim 2 wherein the lighting system includes a plurality of light sources arranged in a hemispherical array.

12. The system of claim 2 wherein the lighting system includes a plurality of light sources arranged in a spherical array.

13. The system of claim 1 wherein the computer processing system is configured to directly compute the variance $\sigma^2$ from a total energy for each point on the surface of the object based on the images captured by the image capture system by substantially computing $$\frac{L_2}{L_0} - \frac{L_1^2}{L_0^2},$$

where $L_0$ is the image of the object acquired under a constant spherical illumination condition, $L_1$ is the image acquired under a linear gradient illumination condition, and $L_2$ is the image acquired under a quadratic gradient illumination condition.

14. The system of claim 1 wherein the lighting system is configured such that all of the images on which the computation of specular roughness is based were illuminated with an illumination pattern having an intensity gradient having an order of no more than one.

15. The system of claim 1 wherein the computer processing system is configured to compute a reflectance function at each point and to analytically fit a cosine lobe to each reflectance function.

16. The system of claim 15 wherein the cosine lobe is a hemispherical cosine lobe of substantially the form $f(\Theta) = k(\hat{\alpha} \cdot \Theta)^n$, where $\Theta$ is a direction, k is the overall intensity of the cosine lobe, $\hat{\alpha}$ is the axis of the cosine lobe, and n is the exponent of the cosine lobe.

17. The system of claim 15 wherein the cosine lobe is a spherical cosine lobe of the substantially form $$f(\Theta) = k\left(\frac{1}{2}\hat{\alpha} \cdot \Theta + \frac{1}{2}\right)^n,$$

where $\Theta$ is a direction, k is the overall intensity of the cosine lobe, $\hat{\alpha}$ is the axis of the cosine lobe, and n is the exponent of the cosine lobe.

18. The system of claim 15 wherein the computer processing system is configured to compute a color channel for each point and for each point and each color channel for each point substantially $o_w$, $o_x$, $o_y$, $o_z$, where $o_w$ is the image of the object acquired under a constant spherical illumination condition, $o_x$ is the image of the object acquired under a linear gradient illumination condition aligned left-to-right, $o_y$ is the image of the object acquired under a linear gradient illumination condition aligned bottom-to-top, and $o_z$ is the image of the object acquired under a linear gradient illumination condition aligned back-to-front.

19. The system of claim 18 wherein the lighting system is configured such that one of the illumination patterns has a single color gradient and wherein the computer processing system is configured to substantially synthesize by $o_x$, $o_y$, $o_z$ by $o_x = o_w \times$ red channel of $o_c$/red channel of $o_w$, $o_y = o_w \times$ green channel of $o_c$/green channel of $o_w$, and $o_z = o_w \times$ blue channel of $o_c$/blue channel of $o_w$, where $o_w$ is the image of the object acquired under a constant spherical illumination condition, and $o_c$ is the image of the object acquired under a linear color gradient illumination condition, with the gradation of red illumination aligned left-to-right, the gradation of green illumination aligned bottom-to-top, and the gradation of blue illumination aligned back-to-front.

20. The system of claim 15 wherein the computer processing system is configured to compute specular roughness substantially based on the following equation:

$$n = \frac{2\|\alpha\| - o_w}{o_w - \|\alpha\|},$$

where $\alpha = \langle 2o_x - o_w, 2o_y - o_w, 2o_z - o_w \rangle$, $o_w$ is the image of the object acquired under a constant spherical illumination condition, $o_x$ is the image of the object acquired under a linear gradient illumination condition aligned left-to-right, $o_y$ is the image of the object acquired under a linear gradient illumination condition aligned bottom-to-top, and $o_z$ is the image of the object acquired under a linear gradient illumination condition aligned back-to-front.

21. The system of claim 15 wherein the computer processing system is configured to compute specular roughness substantially based on the following equation:

$$n = \frac{2\|\alpha\|}{o_w - \|\alpha\|},$$

where $\alpha = \langle 2o_x - o_w, 2o_y - o_w, 2o_z - o_w \rangle$, $o_w$ is the image of the object acquired under a constant spherical illumination condition, $o_x$ is the image of the object acquired under a linear gradient illumination condition aligned left-to-right, $o_y$ is the image of the object acquired under a linear gradient illumination condition aligned bottom-to-top, and $o_z$ is the image of the object acquired under a linear gradient illumination condition aligned back-to-front.

22. The system of claim 15 wherein:
the lighting system is configured such that one of the illumination patterns has an intensity gradient having an order of zero and one of the illumination patterns has an intensity gradient having an order of one; and
the computer processing system is configured to compute the specular roughness of each point on the surface of the object based on the images captured by the image capture system under the illumination of only the illumination pattern with an intensity gradient having an order of one and the illumination pattern having an intensity gradient having an order of zero.

23. The system of claim 1 wherein the computer processing system is configured to compute the specular roughness of each point on the surface of the object based on the images captured by the image capture system under the illumination of only an illumination pattern with an intensity gradient having an order of one and an illumination pattern having an intensity gradient having an order of zero.

24. A system for estimating the specular roughness of points on a surface of an object comprising:
a lighting system configured to illuminate the surface of the object at different times with different illumination patterns, each pattern illuminating the surface from a plurality of different directions;
an image capture system configured to capture an image of the surface of the object when illuminated by each of the different illumination patterns; and
a computer processing system configured to directly compute the specular roughness of each point on the surface of the object based on the images captured by the image capture system without fitting data which is representative of the images to an appearance model.

25. Non-transitory computer readable storage media containing computer-readable programming instructions which, when read and executed by a computer system, cause the computer system to compute the specular roughness of each point on a surface of an object based on images of the surface of the object, each of the surface of the object while illuminated at a different time by a different illumination pattern, each illumination pattern illuminating the surface from a plurality of different directions and forming an intensity gradient having an order of no more than two.

* * * * *